(12) United States Patent
Moy et al.

(10) Patent No.: US 8,591,491 B2
(45) Date of Patent: Nov. 26, 2013

(54) FLOW STOP PROTECTIVE MEANS FOR A FLUID DELIVERY DEVICE OF A MEDICAL PUMP

(75) Inventors: Yei F. Moy, Buffalo Grove, IL (US); Marwan A. Fathallah, Mundelein, IL (US); Steven Pippin, Oak Park, IL (US)

(73) Assignee: Hospira, Inc., Lake Forest, IL (US)

( * ) Notice: Subject to any disclaimer, the term of this patent is extended or adjusted under 35 U.S.C. 154(b) by 0 days.

(21) Appl. No.: 13/539,606

(22) Filed: Jul. 2, 2012

(65) Prior Publication Data
US 2013/0006181 A1 Jan. 3, 2013

Related U.S. Application Data

(60) Provisional application No. 61/503,411, filed on Jun. 30, 2011.

(51) Int. Cl.
*A61B 19/00* (2006.01)
(52) U.S. Cl.
USPC ........................................................ 604/403
(58) Field of Classification Search
USPC .......................................... 604/131, 151, 403
See application file for complete search history.

(56) References Cited

U.S. PATENT DOCUMENTS

| | | | |
|---|---|---|---|
| 5,462,256 A | 10/1995 | Minick et al. | |
| 6,203,528 B1 | 3/2001 | Deckert et al. | |
| 6,231,320 B1 | 5/2001 | Lawless et al. | |
| 6,635,033 B1 | 10/2003 | Hill et al. | |
| 7,258,534 B2 | 8/2007 | Fathallah et al. | |
| 7,766,630 B2 | 8/2010 | Fathallah et al. | |
| 2005/0063831 A1* | 3/2005 | Fathallah et al. | 417/63 |
| 2006/0070669 A1* | 4/2006 | Mabry et al. | 137/625.18 |
| 2007/0038188 A1* | 2/2007 | Bialecki et al. | 604/164.08 |
| 2008/0039824 A1 | 2/2008 | Fathallah et al. | |
| 2010/0057058 A1* | 3/2010 | Ziegler et al. | 604/890.1 |
| 2010/0094224 A1 | 4/2010 | Fathallah et al. | |

FOREIGN PATENT DOCUMENTS

| | | |
|---|---|---|
| WO | 0057941 | 10/2000 |
| WO | 2005030299 | 4/2005 |

OTHER PUBLICATIONS

International Search Report for Application No. PCT/US12/45198, issued Sep. 28, 2012.

\* cited by examiner

*Primary Examiner* — Aarti B Berdichevsky
(74) *Attorney, Agent, or Firm* — Michael R. Crabb

(57) ABSTRACT

A fluid delivery device such as a cassette removably disposed in a medical pump to control fluid flow in the medical pump. The fluid delivery device has an elongated main body including an inlet, an outlet, and a fluid passage extending from the inlet to the outlet. A flow stop is pivotally mounted to the main body for selectively allowing and stopping fluid flow from the fluid passage to the outlet. The fluid delivery device can have various features including the flow stop having grooved sections, a T-shaped collar on the main body inlet or a flange on the main body to prevent inadvertent engagement of the flow stop during removal of the fluid delivery device from the medical pump.

12 Claims, 42 Drawing Sheets

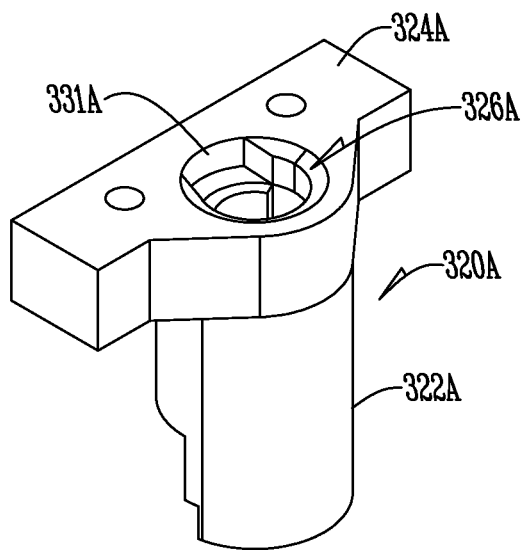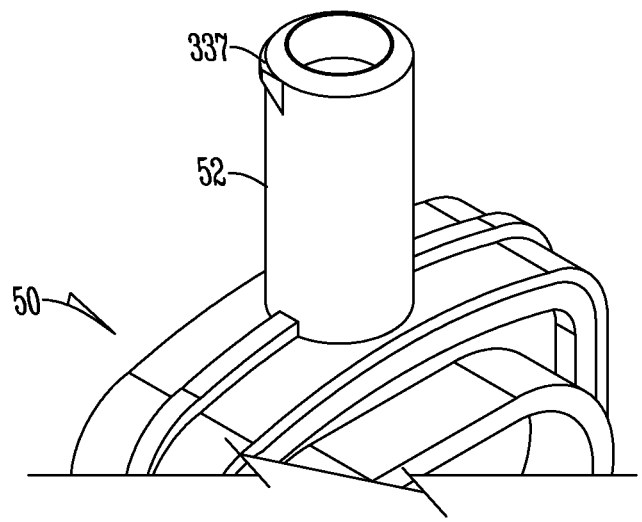
Fig. 30A

FLOW STOP PROTECTIVE MEANS FOR A FLUID DELIVERY DEVICE OF A MEDICAL PUMP

CROSS REFERENCE TO RELATED APPLICATION

This application claims the benefit of U.S. Provisional Application No. 61/503,411 filed Jun. 30, 2011.

BACKGROUND OF THE INVENTION

The present invention relates to means for preventing unrestricted, uncontrolled or inadvertent fluid flow that might otherwise occur as a result of loading or unloading fluid administration tubing sets in a medical pump. More particularly, the present invention relates to means for preventing unrestricted, uncontrolled or inadvertent "free flow" from a cassette, fluid administration set, or other fluid delivery device equipped with a movable flow stop as it is loaded into or removed from a medical pump.

Modern medical care often involves the use of medical pump devices to deliver fluids and/or fluid medicine to patients. Medical pumps permit the controlled delivery of fluids to a patient, and such pumps have largely replaced gravity flow systems, primarily due to the pump's much greater accuracy in delivery rates and dosages, and due to the possibility for flexible yet controlled delivery schedules. Of the modern medical pumps, those incorporating a diaphragm cassette are often preferred because they provide more accurately controlled rate and volume than do other types of pumps.

A typical positive displacement pump system includes a pump device driver and a fluid delivery device, including but not limited to a syringe, tubing, section of tubing, or a disposable cassette. The disposable cassette, which is adapted to be used only for a single patient and for a limited time, is typically a small plastic unit having an inlet and an outlet respectively connected through flexible tubing to a fluid supply container and to the patient receiving the fluid. The cassette includes a pumping chamber, with the flow of fluid through the chamber being controlled by a plunger activated in a controlled manner by the device driver against an elastomeric membrane or flexible diaphragm covering the pumping chamber.

Typically, when the cassette is loaded into the pump a normally closed flow stop on the cassette prevents the free flow of IV fluid either out of the pump onto the floor or improperly to a patient. This unintended, unrestricted, or uncontrolled flow problem is often described as "free flow." Specifically, normally the pivotal flow stop of the cassette is closed and prevents such free flow until a cassette is properly installed in the pump and the cassette loader door is completely closed. At that point one side of the pivotal flow stop is operatively engaged by a pressure sensing distal pin in the pump. This leaves the flow stop in its normally closed position, but under the control of the pumping mechanism via the plunger and the passive outlet valve within the cassette. When the plunger pushes on the pumping chamber and sufficient pressure is generated therein, the outlet valve opens and allows fluid to flow. The pressure in the cassette just downstream from the outlet valve urges the flow stop pressure sensing distal pin upward as fluid is allowed to flow through the outlet of the cassette. Thus, once the cassette is properly installed in the pump, the pumping mechanism controls the opening and closing of the outlet valve and flow from the cassette.

Problems occur with the flow stop in a cassette when a cassette is mis-loaded or when a user prematurely pulls on the tubing upstream of the pump and yanks the cassette out of the pump before the cassette loader door is fully opened. As a result the flow stop can inadvertently come into contact with the distal pin, plunger or other components of the pumping mechanism or pump chassis, thereby causing the flow stop to be pivoted opened into a free flow position. Such free flow is undesirable.

Therefore, a first object of the present invention is to provide a fluid delivery device, such as a cassette or the like, for a medical pump having improved means for preventing free flow during installation and removal of the fluid delivery device.

Yet another object of the present invention is to provide enhanced means for preventing free flow that are simple and inexpensive to manufacture.

Yet another object of the present invention is to provide means on a cassette assembly that prevent pulling of the cassette assembly from a medical pump until the loader mechanism of the pump is fully open.

These and other objects will become apparent to those skilled in the art

BRIEF SUMMARY OF THE INVENTION

A fluid delivery device such as a cassette is removably disposed in a medical pump to control fluid flow in the medical pump. The fluid delivery device has an elongated main body including an inlet, an outlet, and a fluid passage extending from the inlet to the outlet. A flow stop is pivotally mounted to the main body for selectively allowing and stopping fluid flow from the fluid passage to the outlet. The fluid delivery device has preventing means that prevents opening engagement of the flow stop during removal of the fluid delivery device from the medical pump.

A first embodiment is provided associated where a groove is disposed in raised sections of the flow stop that prevents the flow stop from contact with components of the medical pump during removal of the cassette from the main carriage thus preventing unintended movement of the flow stop causing unintended free flow.

Another aspect of the invention in one embodiment is that it provides an orientation and blocking collar at the upper or inlet end of the cassette. The collar is sized, shaped and arranged such that it will contact portions of the pump so that the fluid delivery device cannot be pulled from the medical pump until the cassette loader of the pump is fully open. Furthermore, the collar ensures that the flow stop is properly aligned and not opened by inadvertent contact with various components of the pump during installation and removal.

A final embodiment provides a flange that extends from the fluid delivery device adjacent the inlet. The flange is approximately the width of the fluid delivery device and height of the flow stop to ensure it will contact portions of the pump so that the fluid delivery device cannot be pulled from the medical pump until the cassette loader of the pump is fully open. Thus, the flange ensures that the flow stop is not opened by inadvertent contact with various components of the pump during installation and removal.

BRIEF DESCRIPTION OF THE DRAWINGS

FIG. 30A is an enlarged exploded perspective view of a portion of a cassette and collar of the present invention;

DETAILED DESCRIPTION OF THE PREFERRED EMBODIMENT

Figure 1:
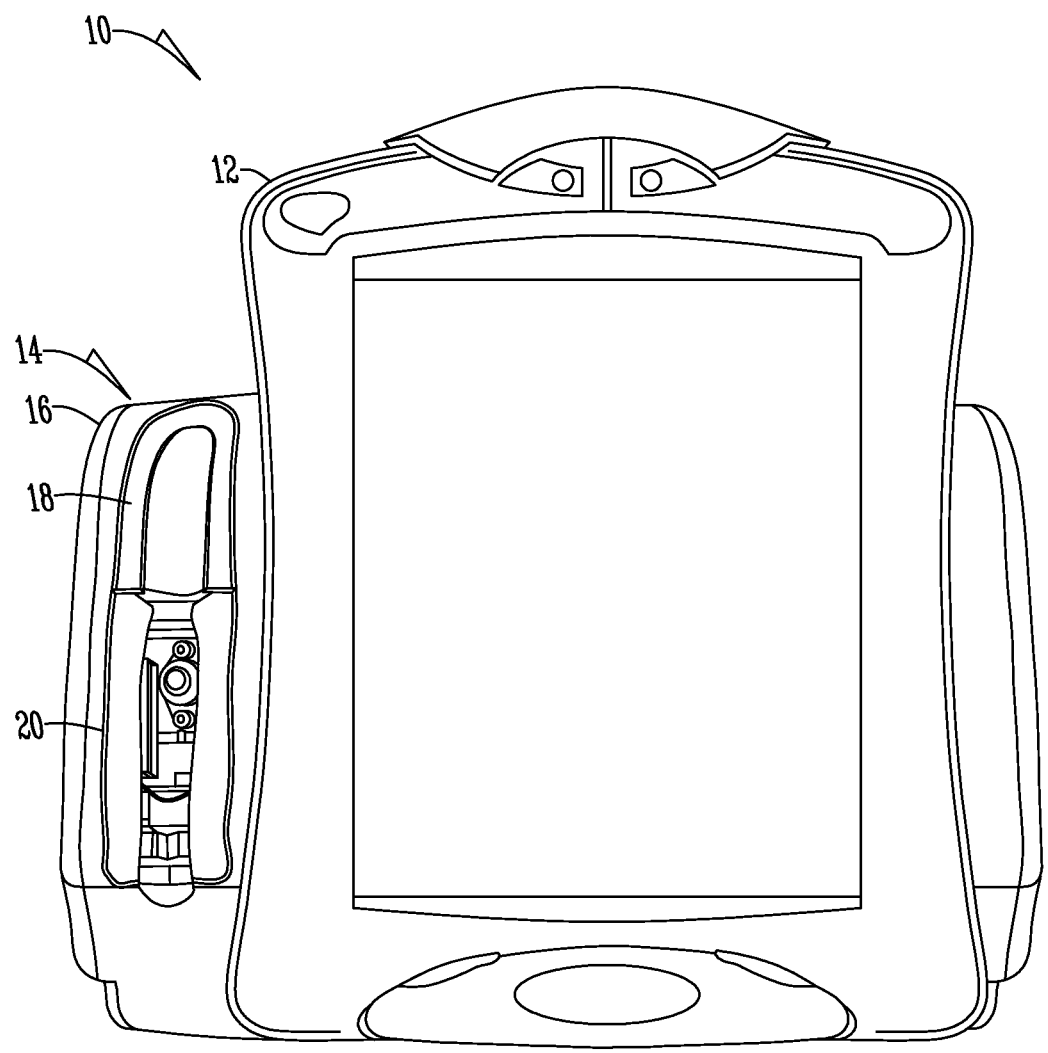
FIG. 1 is a front view of the medical pump of the present invention.

With reference to FIG. 1, a medical pump 10 is shown having a housing 12 and an infuser mechanism 14 attached to the housing 12. The infuser mechanism 14 includes an infuser cover 16, an indicator window 18 attached to the infuser cover 16, and a loader 20 for a fluid delivery device, including but not limited to a cassette, syringe, and/or tubing. The loader 20 is attached to the infuser cover 16 immediately below the indicator window 18.

Figure 2:
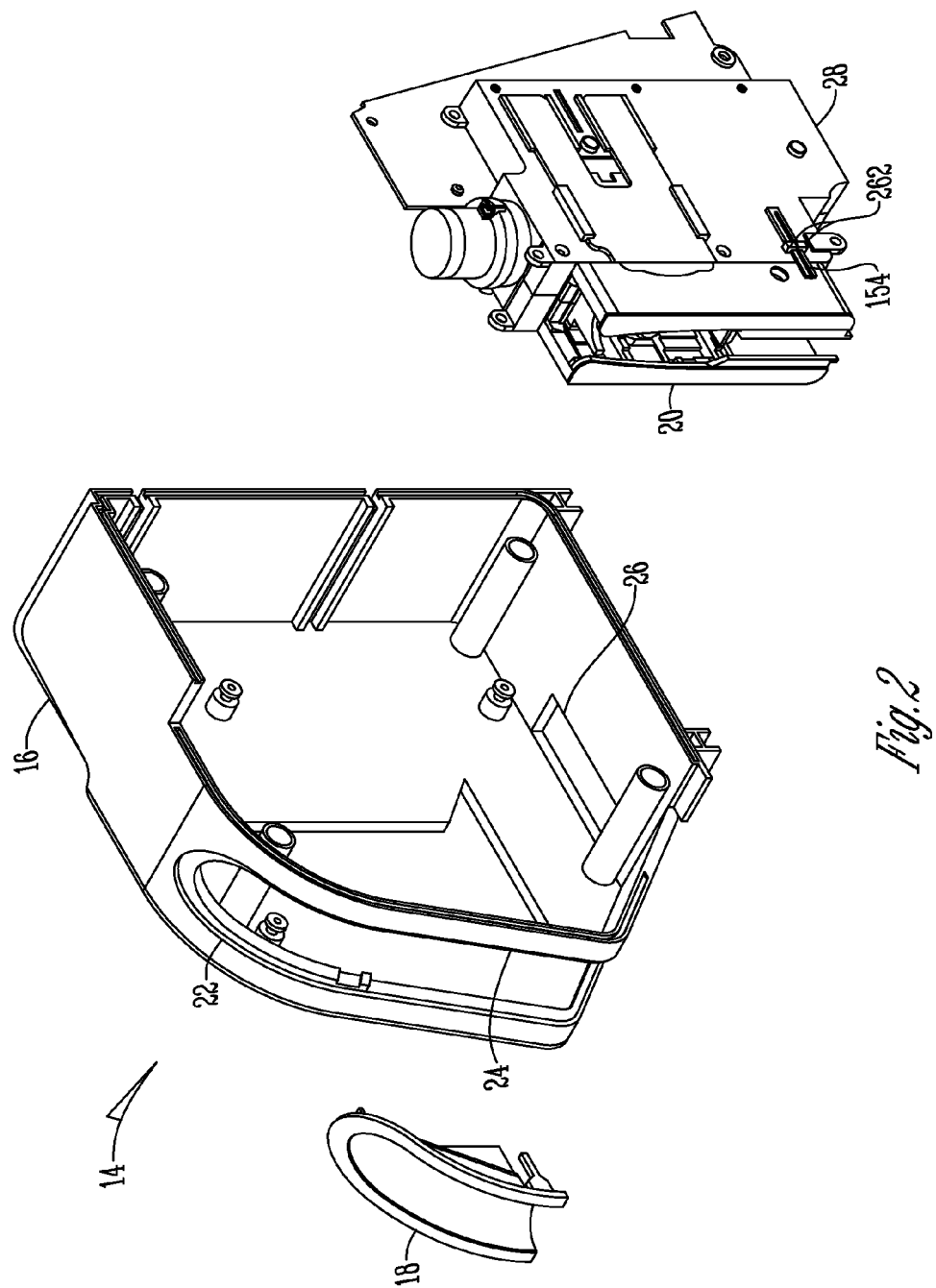
FIG. 2 is an exploded perspective view of an infuser mechanism of the present invention.

With reference to FIG. 2, indicator opening 22, loader opening 24, and manual release opening 26 are all formed in the infuser cover 16. The indicator opening 22 permits insertion and attachment of the indicator window 18 to the infuser cover 16. Likewise, the loader opening 24 permits insertion and attachment of the loader 20 to the infuser cover 16. The manual release opening 26 permits insertion and attachment of a manual release portion 28 of the loader 20 to the infuser cover 16.

Figure 3:
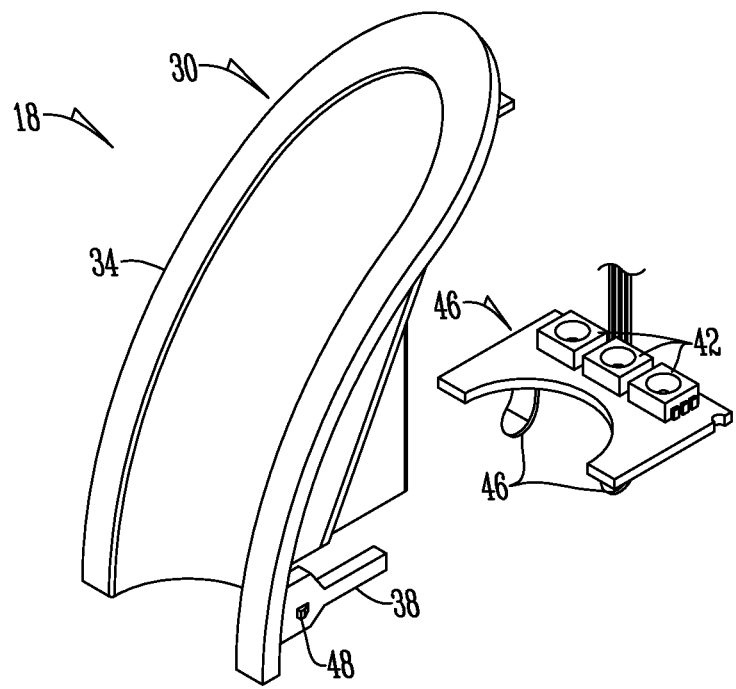
FIG. 3 is an exploded perspective view of an indicator window of the present invention.
Figure 4:
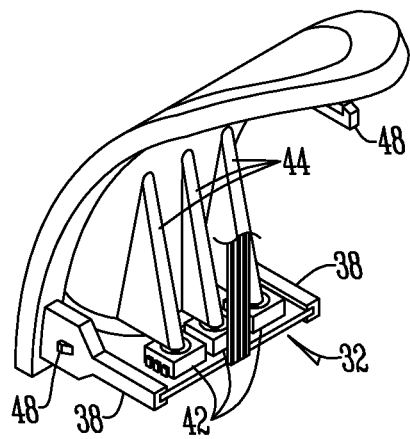
FIG. 4 is a rear perspective view of an indicator window of the present invention.

With reference to FIGS. 3 and 4, a window body 30 and light assembly 32 form the indicator window 18. The window body 30 is formed of a transparent or translucent material which facilitates the diffusion and transmission of light therethrough. The window body 30 has an outer surface 34 that includes a groove shaped portion 36. The groove shaped portion 36 is shown as being concave, but may be formed in any suitable shape. The groove shaped portion 36 provides clearance for a user to smoothly route an inlet tube (not shown) to the loader 20.

A pair of rails 38 extends horizontally from an inner surface of the window body 30. The rails 38 secure the light assembly 32 to the window body 30. Several multi-color indicator elements 42 are located on the upper surface of the light assembly 32. These indicator elements 42 are shown as three individual light-emitting diode (LED) lights. The indicator elements 42 are each associated with corresponding light pipes 44.

The light pipes 44 are formed as an integral portion of the inner surface 40 of the window body 30. The light pipes 44 facilitate the even distribution of light from the indicator elements 42 to the outer surface 34 of the window body 30. Due to the multi-color attributes of the indicator elements 42, the outer surface 34 of the window body 30 can be lit up with various colors, and can continuously or intermittently be lit. The coloring and/or flashing is used to provide an indication of the operation conditions of the pump 10.

One or more illumination elements 46 are located on the lower surface of the light assembly 32. These illumination elements 46 are shown as two individual white light LEDs. When the loader 20 is opened for insertion of a cassette, the illumination elements 46 are activated to illuminate the area where the cassette is inserted into the pump 10. The illumination elements 46 may immediately light up or may be designed to gradually illuminate upon opening of the loader 20. The determination of when the loader 20 has been opened will be discussed in greater detail below.

Several snap fasteners 48 extend from the inner surface 40 of the window body 30. These snap fasteners 48 secure the indicator window 18 to the infuser cover 16 in covering relation to the indicator opening 22.

Figure 5:
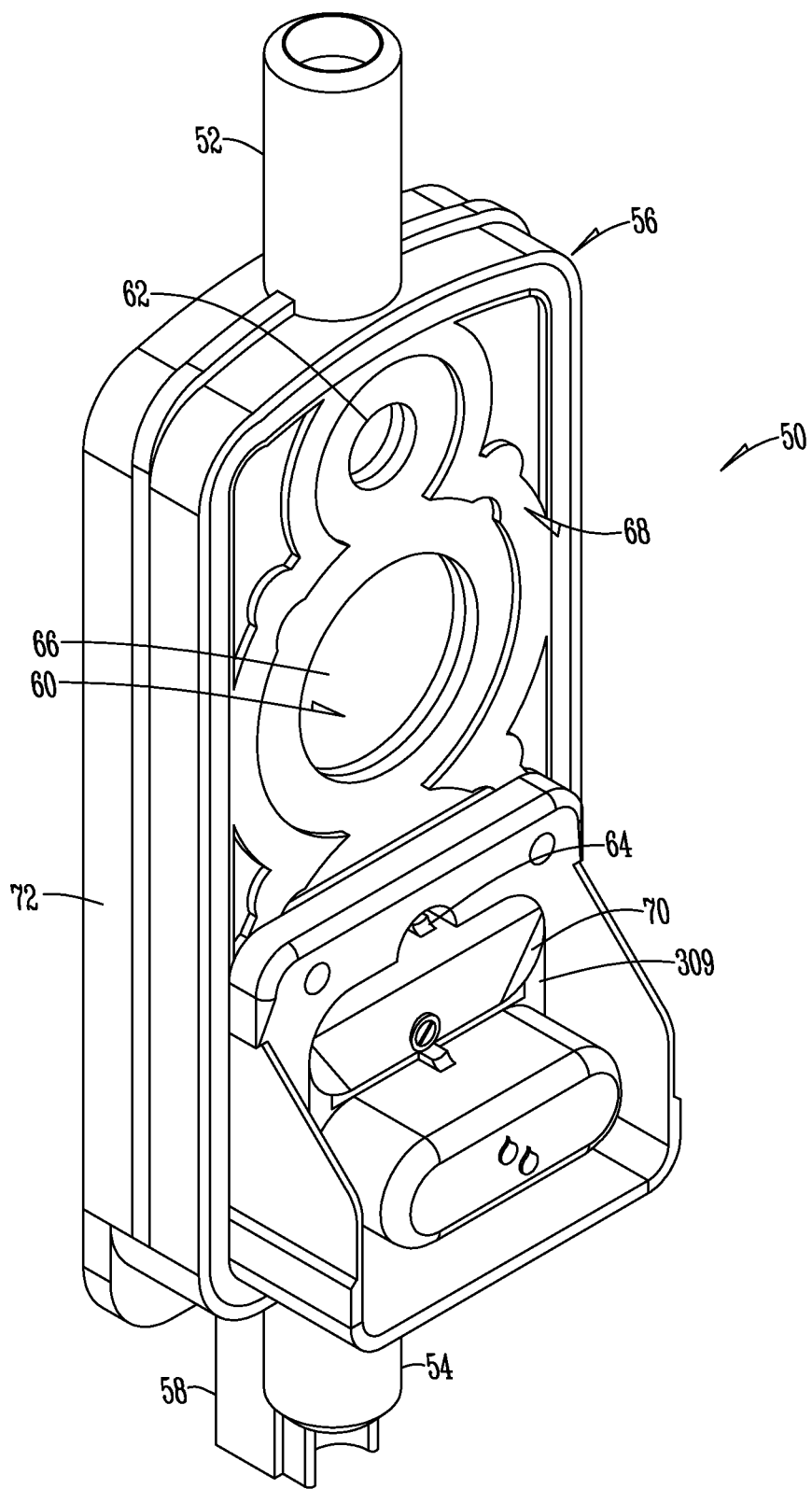
FIG. 5 is a perspective view of a prior art cassette for use with the present invention.

With reference to FIG. 5, one fluid delivery device, such as a cassette 50, suitable for use with the present invention is shown. The cassette 50 includes an inlet 52 and an outlet 54 formed in main body 56. Attached to the outlet 54 is a tube support element 58 for ensuring that tubing (not shown) connected to the outlet 54 is maintained in a proper position with respect to external sensors (not shown).

Figure 19:
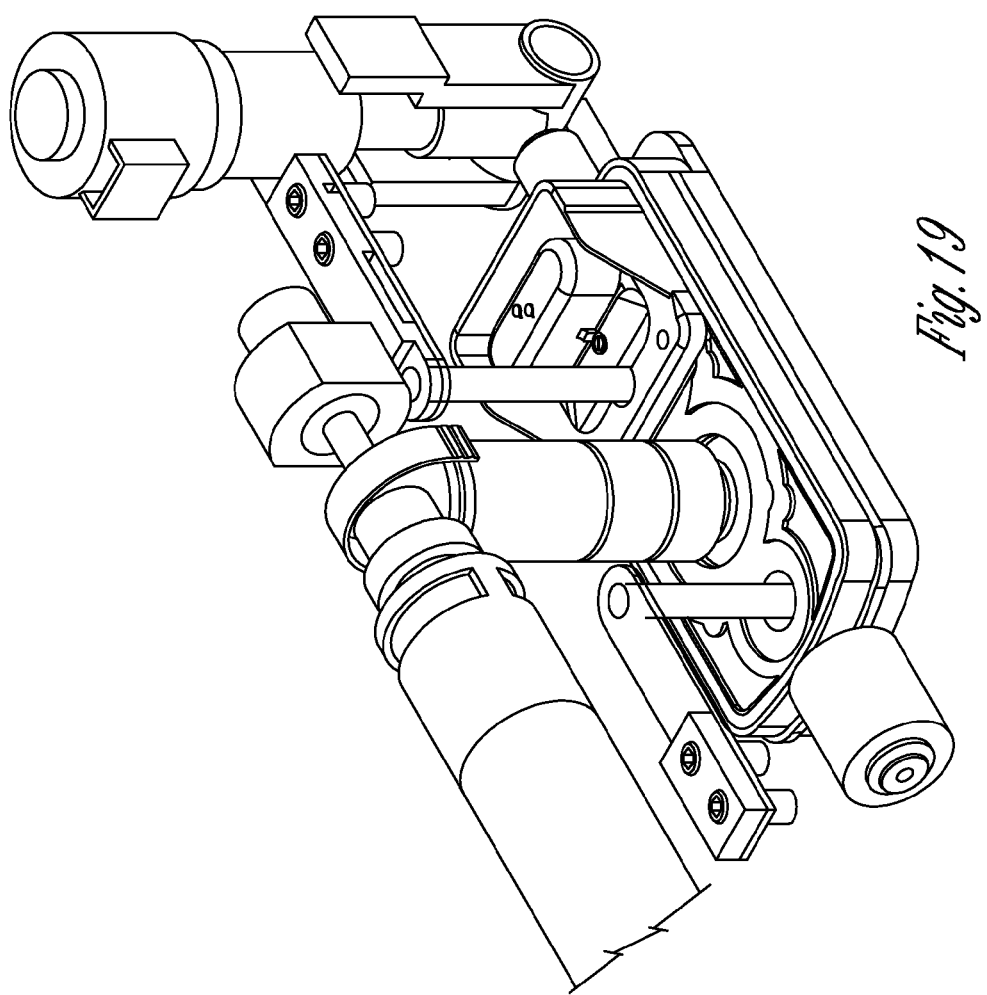
FIG. 19 is a prior art cut away plan view of a cassette engaged by pump components.

An elastomeric membrane 60 forms an inlet diaphragm 62, an outlet diaphragm (generally indicated at 64 in FIG. 5 and better understood in view of FIGS. 19 and 20), and a pumping chamber 66 located between the inlet and outlet diaphragms 62 and 64 on an inner face 68 of the main body 56.

Figure 20:
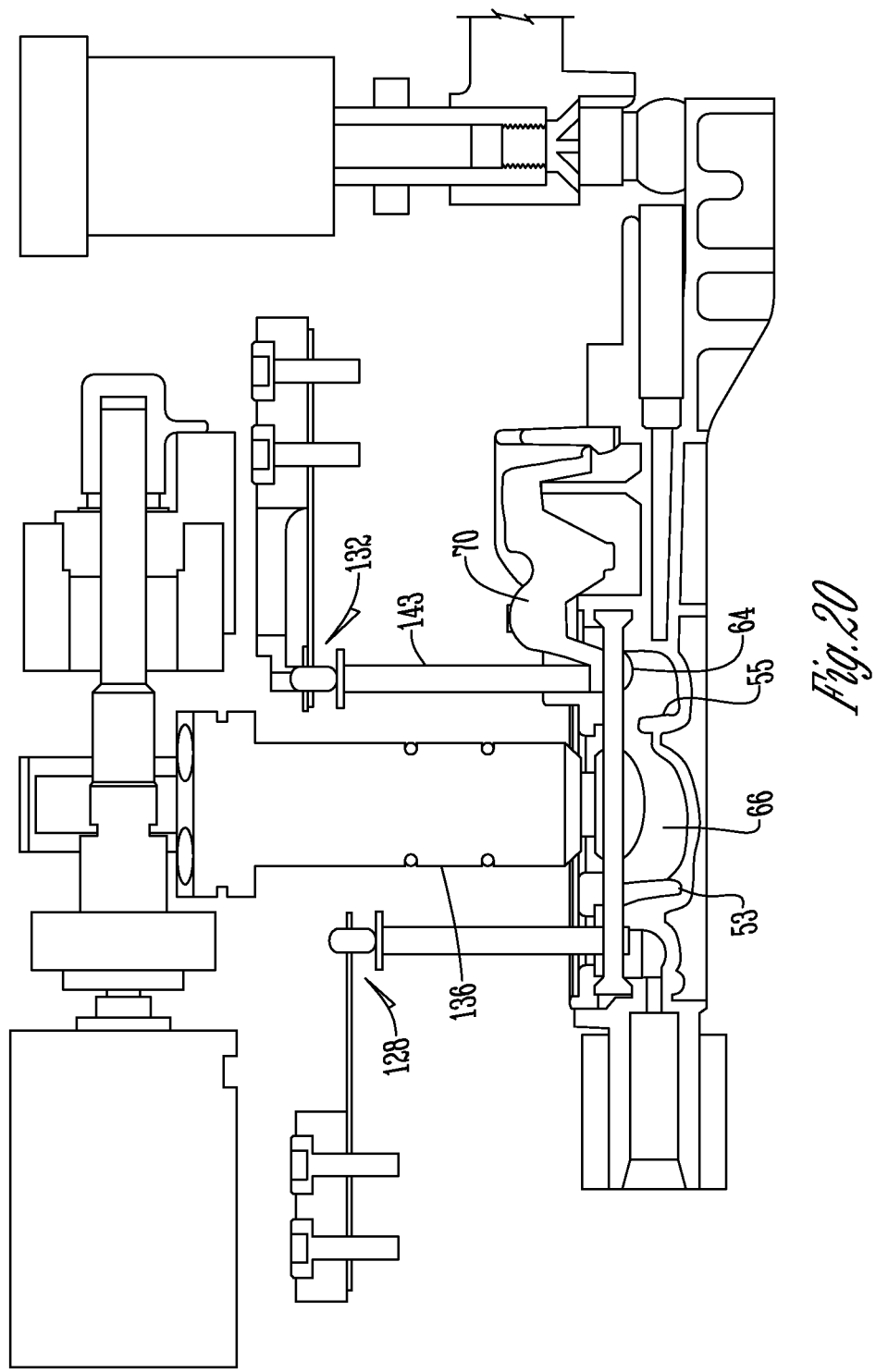
FIG. 20 is a cross sectional view taken along line 20-20 in FIG. 19.

In operation, fluid enters through the inlet 52 and is forced through outlet 54 under pressure. The fluid is delivered to the outlet 54 when the pump 10 displaces the pumping chamber 66 to expel the fluid. During the intake stroke the pump 10 releases the pumping chamber 66, the passive inlet valve 53 (FIG. 20) opens and the fluid is then drawn through the inlet 52 and into the pumping chamber 66. In a pumping stroke, the pump 10 displaces the pumping chamber 66 to force the fluid contained therein through the outlet 54 once pressure in the pumping chamber is sufficient to crack open the passive outlet valve 55 (FIG. 20). Thus, the fluid flows from the cassette 50 in a series of spaced-apart pulses rather than in a continuous flow. The fluid is delivered to the patient at a pre-set rate, in a pre-determined manner, and only for a particular pre-selected time or total dosage.

A flow stop 70 is formed as a pivotal switch in the main body 56 and protrudes a given height from the inner surface 68. This protrusion forms an irregular portion of the inner surface 68 which can be used to align the cassette 50 as well as monitor the orientation of the cassette 50, as will be discussed further below. The flow stop 70 provides a manual switch for closing and opening the cassette 50 to fluid flow and a pressure monitoring device as described in greater detail in U.S. Pat. Nos. 5,462,256 and 5,816,779, which are incorporated by reference in their entirety herein.

A rim 72 is located around the outer surface of the main body 56 and adjacent the inner surface 68. The rim 72 is used to secure the cassette in a fixed position relative to the pump 10.

Figure 6:
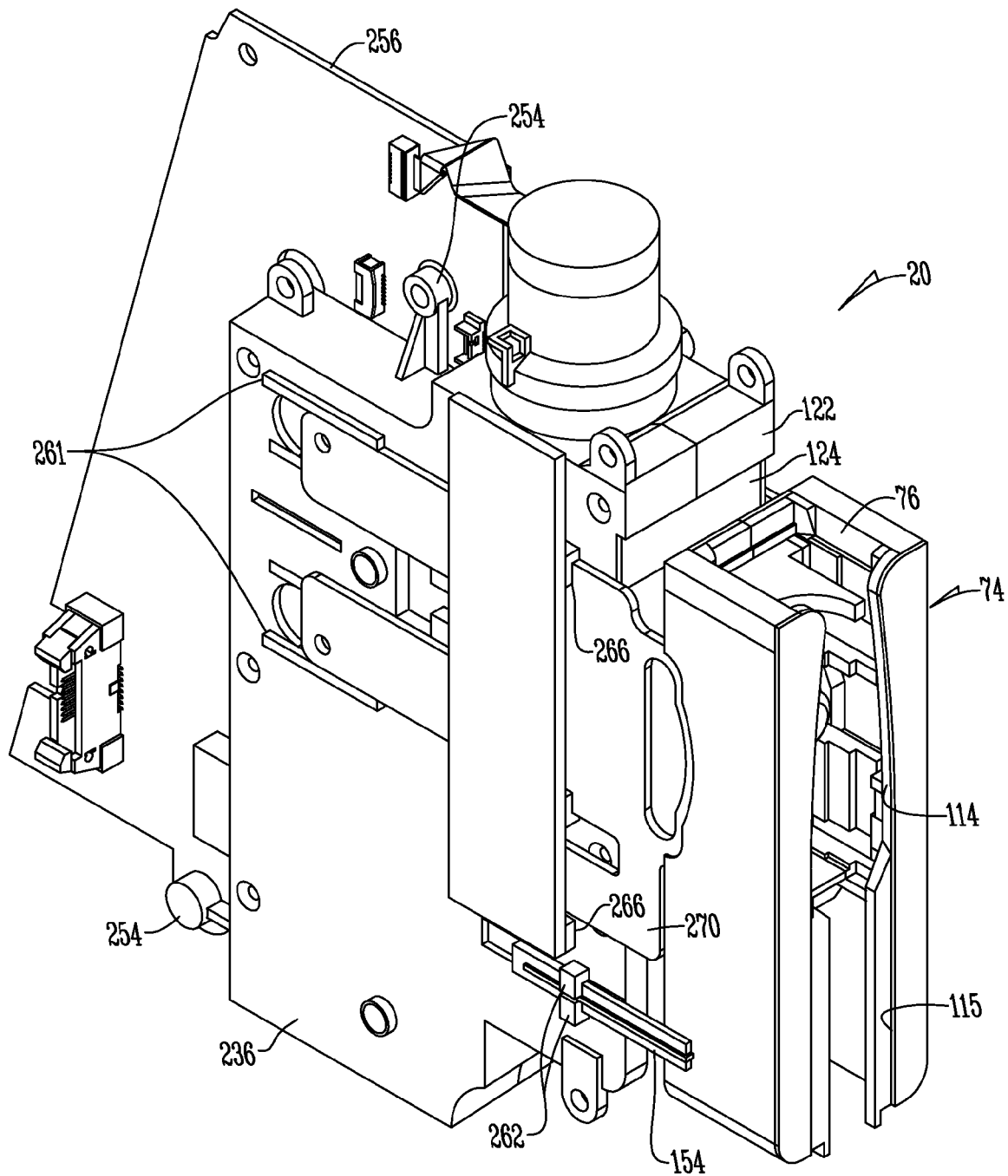
FIG. 6 is a left side perspective view of an open loader with no cassette.

With reference to FIGS. 5 and 6, a front carriage assembly 74 is shown extending from the loader 20. In this extended position, a cassette 50 (not shown) is inserted into a top opening 76 of the front carriage assembly 74.

Figure 7:
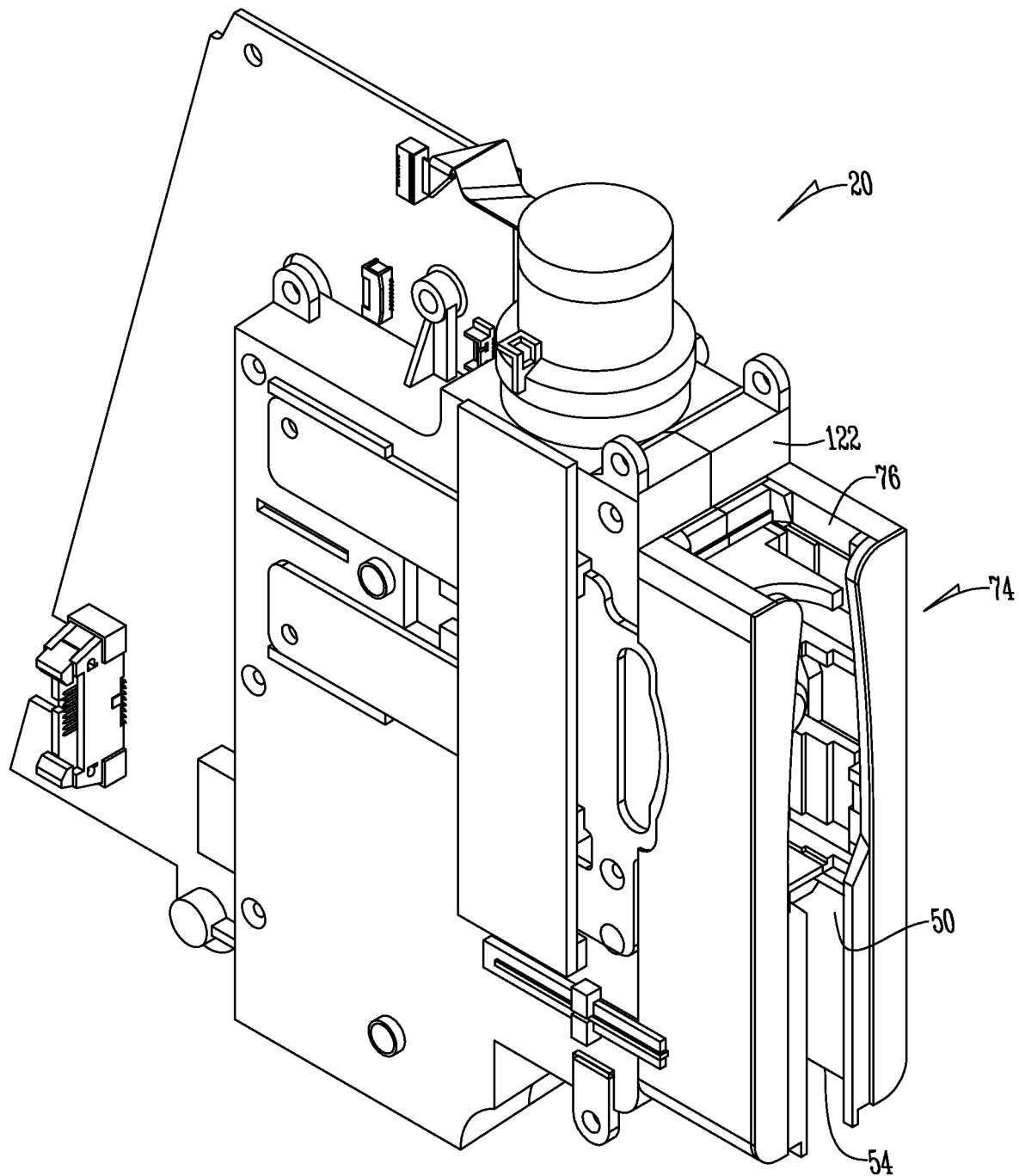
FIG. 7 is a left side perspective view of a closed loader with a cassette.

With reference to FIGS. 5 and 7, the front carriage assembly 74 is shown in a closed position. In proper use, top opening 76 first receives the outlet 54 of the cassette 50 with the inner surface 68 facing towards the loader 20. This proper orientation of the cassette 50 to the loader 20 is essential for proper operation of the pump 10. As will be described in more detail below, the loader 20 of the present invention has been designed to include several mechanical and electronic features to ensure the proper alignment of the cassette 50.

Figure 8:
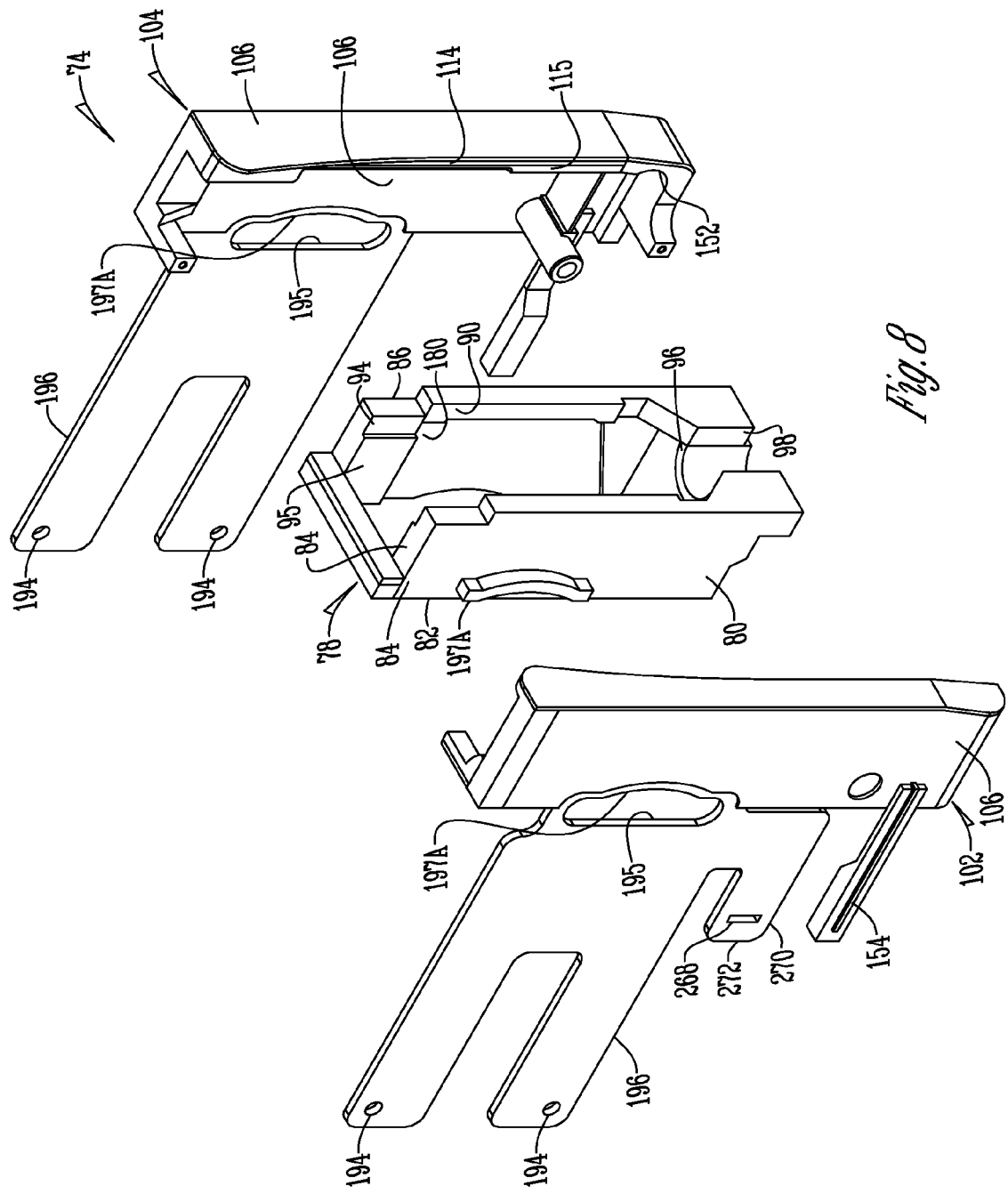
FIG. 8 is a perspective exploded left side view of a front carriage assembly of the present invention.

With reference to FIGS. 5 and 8, a main carriage 78 having a main body 80 with a top opening 81 therein for receiving a cassette 50 as well as an open base surface 82 which permit access to the inner surface 68 of the cassette 50. Left and right vertical side walls 84 and 86 extend horizontally from the base surface 82. Outer lips 88 are positioned opposite the base surface 82 on the end of each side wall 84 and 86. The outer lips 88 define an outer opening 90 in the main body 80. The outer lips 88 abut the rim 72 of an inserted cassette 50 to prevent the cassette 50 from falling out of the outer opening 90, and also enable the main carriage 78 to press the cassette 50 towards the loader 20 by engaging the rim 72.

A cassette footing 92 is formed from portions of the side walls 84 and 86 and the outer lips 88. The cassette footing 92 restricts movement of the cassette 50 within the main carriage 78 to hold the cassette 50 in a desired position with respect to the loader 20. A lateral support 94 is formed in each side wall 84 and 86 for receiving the rim 72 and restricting the lateral movement of the rim 72. An inner lip 95 is formed in each side wall 84 and 86 for restricting the horizontal movement of the inner surface 68 by engaging the rim 72. A lower support 96 is formed between the side walls 84 and 86 to support the cassette 50 in the main carriage 78. An outlet support lip 98 is formed at the lower end of outer opening 90 to fit around and restrict the movement of the cassette outlet 54.

The front carriage assembly 74 includes left and right front fascia 102 and 104 that hold the main carriage 78 and attach the main carriage 78 to the rest of the loader 20. Each front fascia 102 and 104 has a main body 106 with a side opening 108 for receiving the main carriage 78 therein.

With reference to FIGS. 5, 6 and 8, the front fascia 102 and 104 form openings which correspond to matching openings in the main carriage 78. Thus the front fascia 102 and 104 has outer opening 114, inner opening 116, and defines the top opening 76. The outer opening 114 adjoins the outer opening 90 of the main carriage 78 and permits a user to see that a cassette 50 is contained within the front carriage assembly 74. A tube support opening 115 is formed at the lower end of outer opening 114 to fit around and restrict the movement of the tube support 58. The inner opening 116 adjoins open base surface 82 and permits access to the inner surface 68 of the cassette 50.

Figure 9:
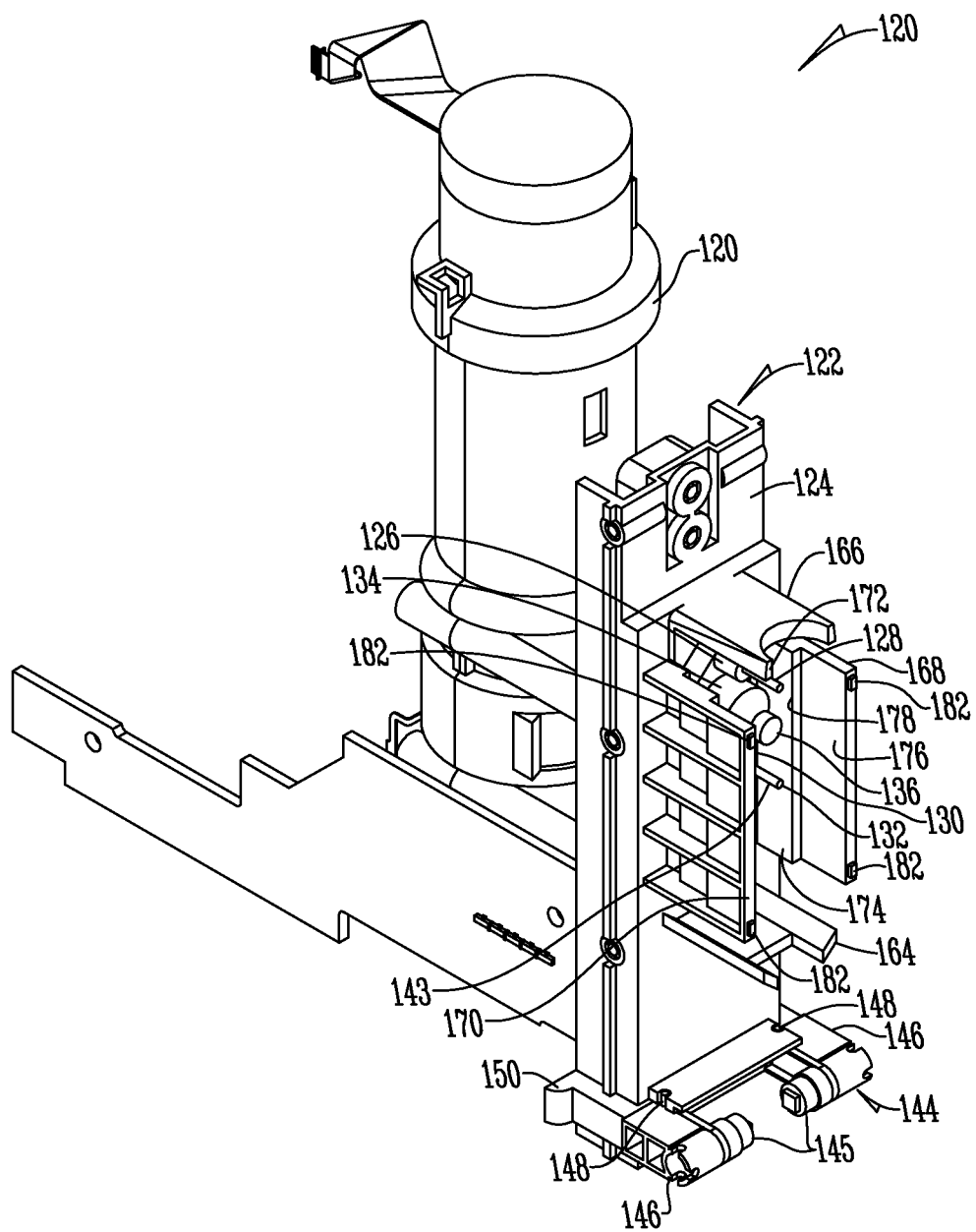
FIG. 9 is a perspective left side view of the pump chassis assembly.

With reference to FIG. 9, a pump chassis assembly 120 is shown. The pump chassis assembly 120 has a main chassis 122 with a vertically disposed base surface 124. The base surface 124 has an opening 126 permitting an inlet or proximal pressure sensor 128 to pass through the base surface 124 and extend horizontally therefrom. An opening 130 in the base surface 124 is positioned below the inlet pressure sensor 128 and permits an outlet or distal pressure sensor 132 to pass through the base surface 124 and extend horizontally therefrom. An opening 134 in the base surface 124 is positioned between the inlet pressure sensor 128 and the outlet pressure sensor 132 and permits a plunger 136 to pass through the base surface 124 and extend horizontally therefrom. A motor 142 is connected to the plunger 136 for driving (or reciprocating) the plunger back and forth.

An opening 138 in the base surface 124 is positioned below the outlet pressure sensor 132 and permits an orientation sensor 140 to pass through the base surface 124 and be positioned flush with the base surface 124. The orientation sensor 140 is shown as an infrared reflective sensor which determines the distance to the cassette 50. The orientation sensor 140 is located to detect the presence or absence of flow stop 70 as an irregular portion of the inner surface 68. The detection of the presence or absence of flow stop 70 is used to align the cassette 50 as well as monitor the orientation of the cassette 50.

With reference to FIGS. 5, 9, 13, 19 and 20, once a cassette 50 is fully loaded and the front carriage assembly 74 is closed, the inlet pressure sensor 128 engages the inlet diaphragm 62 of cassette 50. The outlet pressure sensor 132 engages the outlet diaphragm 64. The plunger 136 engages the pumping chamber 66. A flow stop post or distal pin 143 positioned between the outlet pressure sensor 132 and the orientation sensor 140 on the base surface 124 engages the flow stop 70 to ensure it is in a closed position and monitor outlet pressure. The flow stop post 143 prevents free flow of fluid through cassette 50 once the front carriage assembly 74 is closed.

With reference to FIGS. 8 and 9, one embodiment of the present invention is shown with a pair of air sensors 144 including sensor heads 145 attached to the near ends of arms 146. The arms 146 are pivotally secured to the base surface 124 at hinge 148. The arms 146 are spring biased to pull the air sensors 144 together. A cam element 150 extends horizontally from the far end of each arm 146.

An air sensor slot 152 is formed in each front fascia 102 and 104 to receive the near ends of arms 146 as the front carriage assembly 74 moves in and out with respect to the main chassis 122. Air cam plates 154 extend horizontally from each front fascia 102 and 104 to engage and drive the cam elements 150 of the air sensors 144.

When the front carriage assembly 74 is fully extended, an open portion 156 of each air cam plate 154 forces the cam elements 150 inward, pivoting the arms 146 about the hinges 148 and moving the sensor heads 145 apart. When the front carriage assembly 74 is fully withdrawn, a closed portion 158 of each air cam plate 154 allows the spring biased cam elements 150 to move outward, pivoting the arms 146 about the hinges 148 and moving the sensor heads 145 together. A ramp portion 160 of each air cam plate 154 is located between the open portion 156 and the closed portion 158 of each air cam plate 154 for providing a smooth transition for the cam element 150 as it moves from the open portion 156 to the closed portion 158.

The outward movement of the sensor heads 145 is required to allow effluent tubing (not shown) attached to the cassette outlet 54 to be received between the sensor heads 145. The inward movement of the sensor heads 145 is required to press the sensor heads 145 together to squeeze the effluent tubing (not shown). This squeezing is necessary for the sensor heads 145 physically contact the effluent tubing (not shown) to get accurate measurements of air contained therein.

Figure 12:
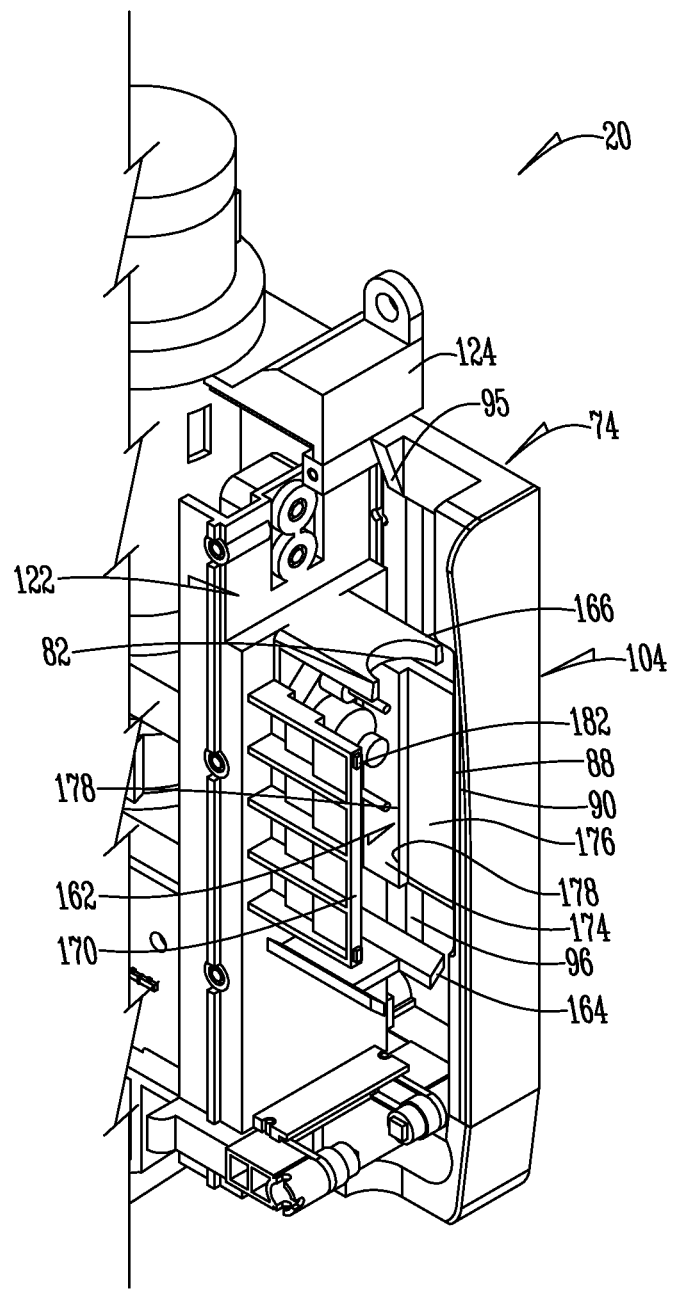
FIG. 12 is a partial sectional left side perspective view of a closed loader with no cassette taken along line 12-12 in FIG. 7, where the left slide assembly is removed and the carriage is in vertical cross section.

With reference to FIGS. 8, 9 and 12, a fixed seat 162 is formed by multiple finger elements 164, 166, 168, and 170 extending horizontally from the vertical base surface 124. The bottom finger element 164 is positioned below the orientation sensor 140 and receives the cassette outlet 54 to restrict the movement of the inlet 54. The top finger element 166 is positioned above the inlet pressure sensor 128 and has an outer end with a groove 172 therein to receive and restrict the movement of the inlet 52. Left and right lateral finger elements 168 and 170 are positioned on either side of the plunger 136.

The top, right and left finger elements 166, 168, and 170 have a finger base 174 attached to the vertical base surface 124, a finger tip 176 extending horizontally from the finger base 174 toward the main carriage 78, and an end stop ledge 178 formed between the finger base 174 and the finger tip 176. Each finger tip 176 is tapered with a narrowed portion facing the main carriage.

Corresponding finger grooves 180 are formed in each side wall 84, 86 for receiving the left and right lateral finger elements 168, 170, respectively, of the main chassis 122. Each groove 180 has a closed end formed by the outer lips 88 for abutting corresponding finger posts 182 formed at outer ends of the finger tips 176.

Figure 10:
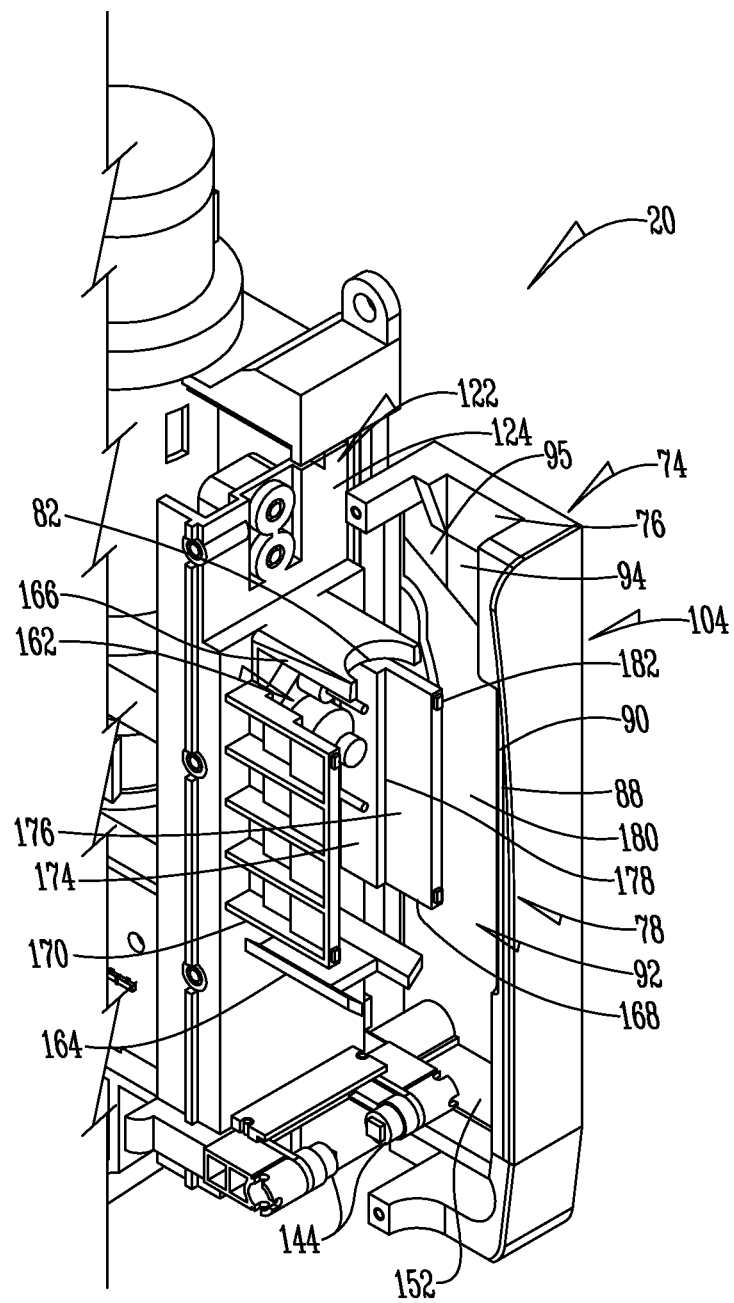
FIG. 10 is a partial sectional left side perspective view of an open loader with no cassette taken along line 10-10 in FIG. 6, where the left slide assembly is removed and the carriage is in vertical cross section.
Figure 11:
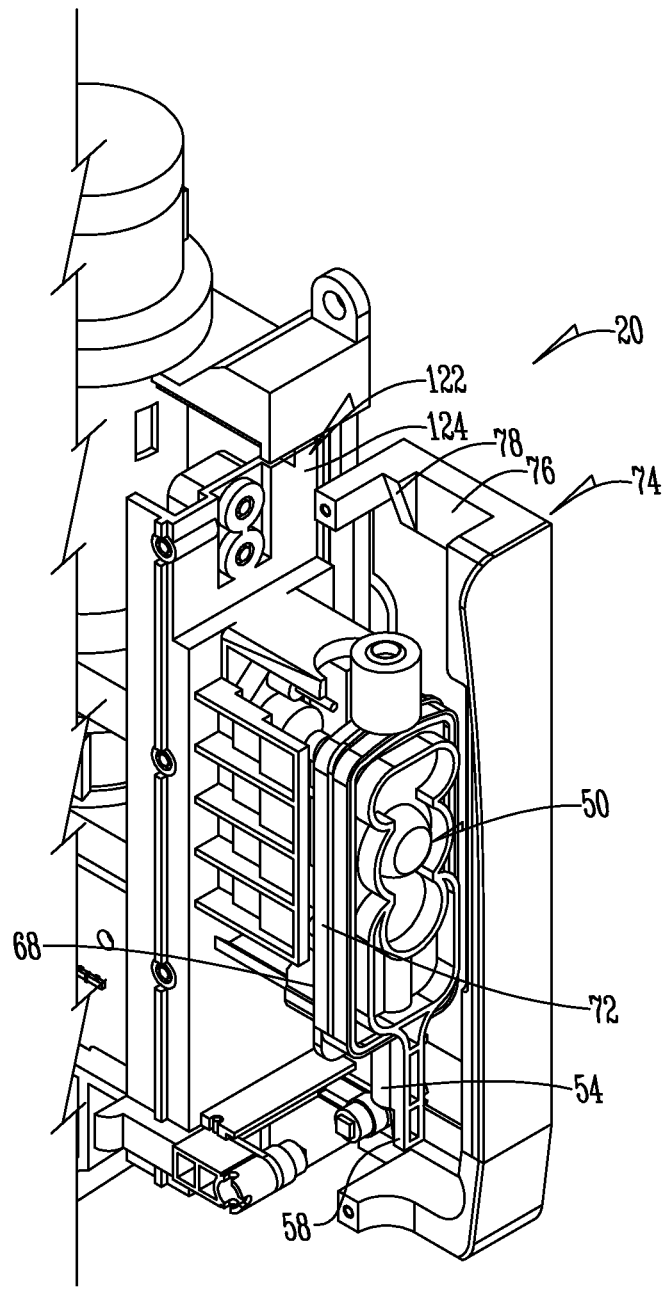
FIG. 11 is a partial sectional left side perspective view similar to FIG. 10, but a prior art cassette is in the open loader.

With reference to FIGS. 10 and 11, in operation the cassette 50 is inserted into top opening 76 of the front carriage assembly 74, when the loader 20 is in the open position. Upon insertion, the cassette 50 slides into the main carriage 78 and is loosely secured in place by cassette footing 92. The lateral support 94 of the cassette footing 92 restricts the lateral movement of the cassette rim 72; the inner lip 95 and the outlet support lip 98 restrict the horizontal movement of the cassette inner surface 68 by engaging the rim 72; and the outlet support lip 98 fits around and restricts the movement of the cassette outlet 54.

Figure 13:
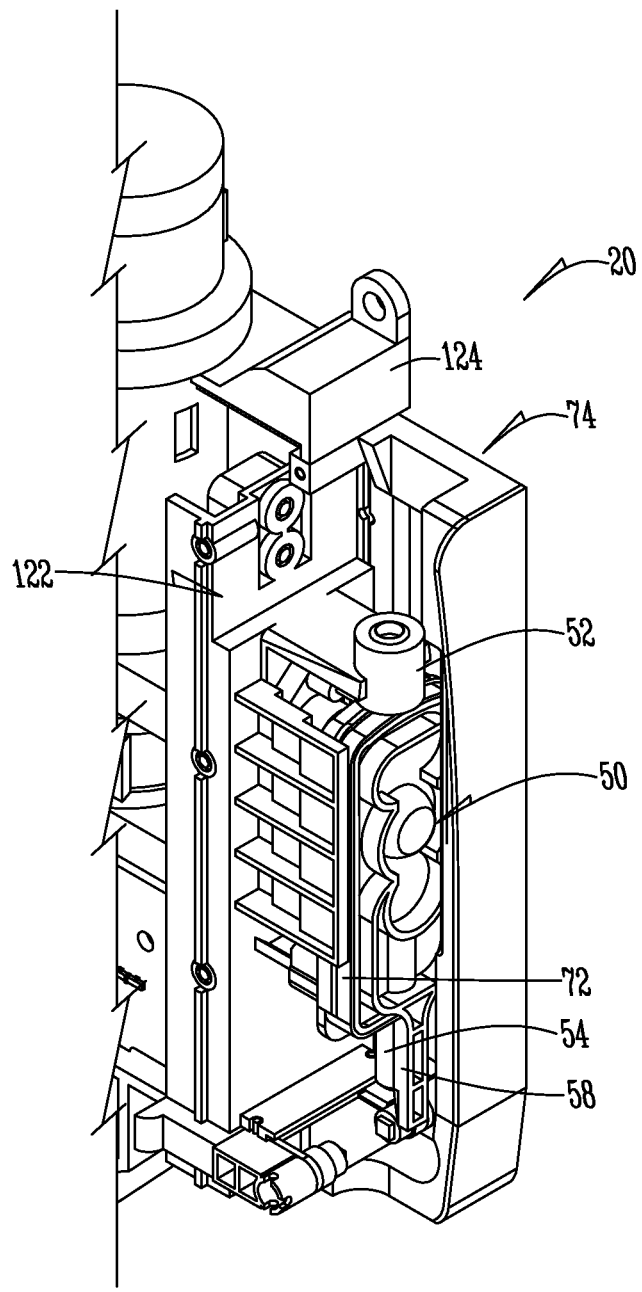
FIG. 13 is a partial sectional left side perspective view similar to FIG. 12, but a prior art cassette is in the closed loader.

With reference to FIGS. 10, 12 and 13, the main carriage 78 is movable from an open position horizontally inwardly with respect to the main chassis 122 to a closed position to engage the cassette 50 to the fixed seat 162. When the loader 20 is loaded with a cassette 50 and closed, the left and right lateral finger elements 168, 170 are received within the finger grooves 180 between the side walls 84, 86 and the cassette 50. The cassette footing 92 permits the cassette 50 to adjust its position within the main carriage 78 while the cassette 50 is being forced onto the fixed seat 162.

Figure 14:
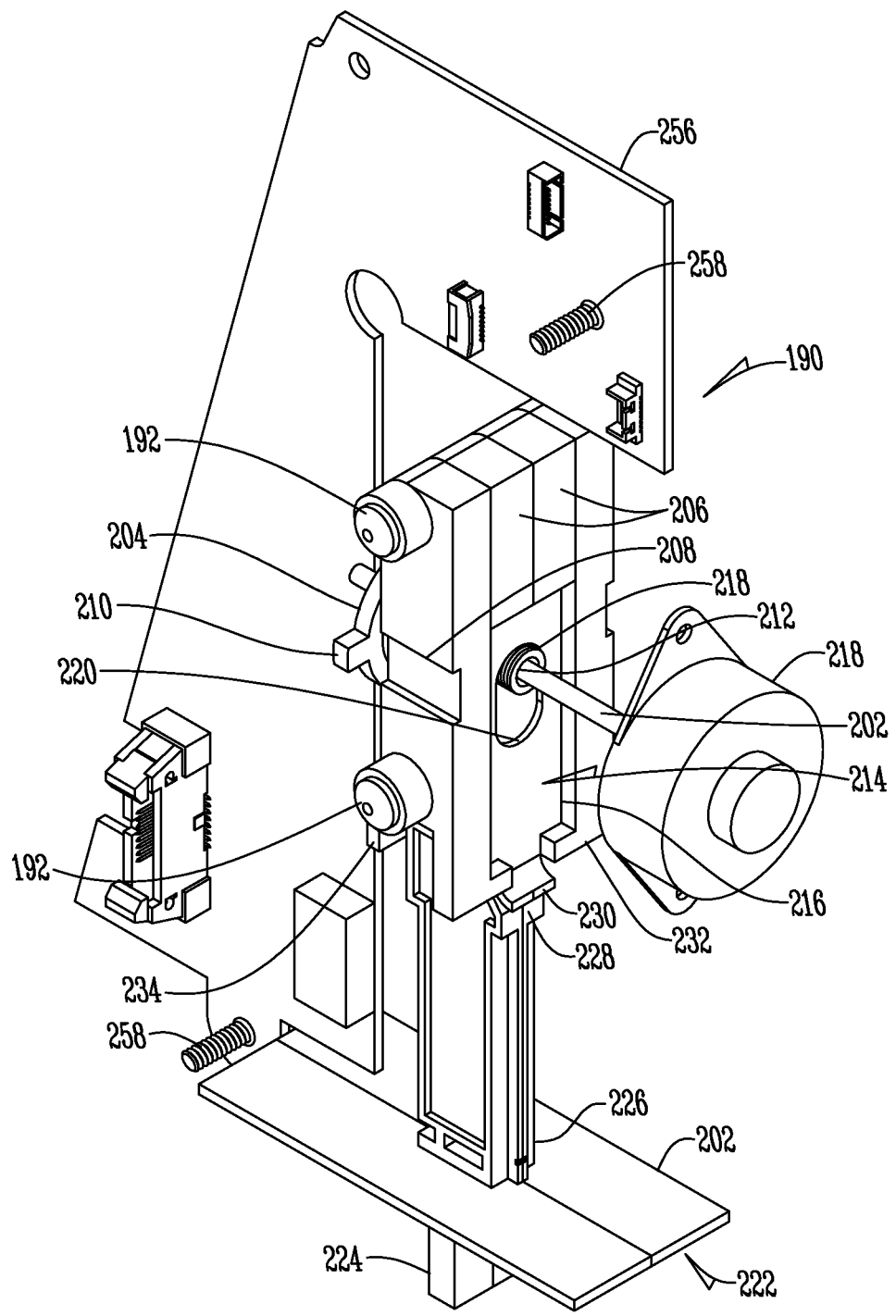
FIG. 14 is a perspective left side view of a manual release, actuator assembly and infuser board.

With reference to FIGS. 8 and 14, a rear carriage assembly 190 has fasteners 192 to connect to fastener receivers 194 formed in side plates 196 of the front carriage assembly 74. Each side plate 196 extends from one of the front fascia 102, 104 towards the rear carriage assembly 190. A clearance opening 195 is formed through each of the side plates 196 and a curved notch 197A is formed in each main body 106 for receiving a corresponding curved post 197B which extends horizontally from each of the side walls 84 and 86 of the main carriage 78. The sets of curved notches 197A and posts 197B allow minor movement of the main carriage 78 within the side openings 108 of the front fascia 102 and 104.

With reference to FIGS. 5, 8 and 10, additionally, the curved posts 197B allow the main carriage 78 to "float" with respect to the main chassis 122. This floating of the main carriage 78 allows the fixed seat 162 to dictate the position of both the main carriage 78 and cassette 50 when the main carriage 78 is in the closed position. Thus the main carriage 78 has rotational freedom on at least one axis with respect to the main chassis 122.

While the embodiment described above is directed to rotational freedom on at least one axis, one of ordinary skill in the art will appreciate that various embodiments that permit rotational freedom on two or even three axes may be provided without departing from the present invention. For instance, it is contemplated that the main carriage 78 could be attached to a gimbal system (not shown) which would allow full XYZ rotational freedom to the main carriage 78 with respect to the main chassis 122.

The finger elements 164, 166, 168, and 170 of the fixed seat 162 dictate the vertical and lateral position of the cassette 50, while carriage is held against posts 182. Posts 182 are the defining features for the inward/outward location of the cassette 50. The lips 88 of the main carriage 78 contact the posts 182 and the rim 72 of the cassette 50 simultaneously, controlling their registration. The rim 72 and posts 182 are both in contact with the same surface of the carriage 78, and therefore are coincident with each other.

One of ordinary skill in the art will appreciate that various embodiments of the finger elements 164, 166, 168, and 170 may be provided without departing from the present invention. For instance, finger element 164 may be provided as a flexible resilient member to provide an upward biasing force on the cassette 50 while also displacing to accommodate some variance in the positioning of the cassette 50. Similarly, finger element 166 may be a flexible resilient member to provide a downward biasing force.

With reference to FIGS. 8 and 14, the rear carriage assembly 190 includes an actuator 198 connected to the main carriage 78 via the side plates 196 to automatically move the main carriage 78 from the open position to the closed position. The actuator 198 is shown as a linear actuator; however other types of drives may be used without departing from the present invention. For instance, a cam plate driven by a DC motor could be used instead of the linear actuator 198 shown here.

Figure 16:
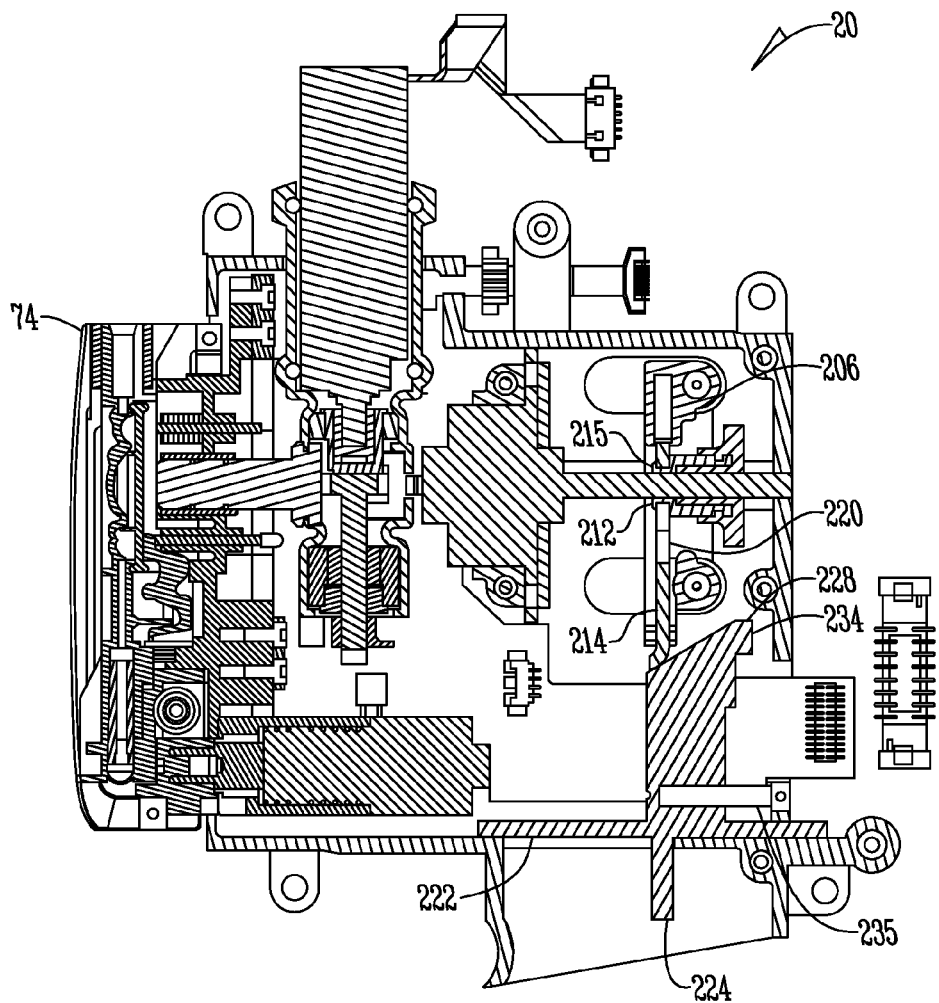
FIG. 16 is a vertical cross sectional side view of the loader in the closed position with a prior art cassette loaded in it.

With reference to FIGS. 14 and 16, a threaded shaft 202 is driven by the actuator 198. As the shaft 202 turns, a nut 204 is tightened or loosened along the length of the shaft 202 (i.e. moves axially). This tightening or loosening of the nut 204 transfers the rotational drive of the actuator 198 into a linear motion to drive the front carriage assembly 74. Left and right plate housings 206 are positioned around the nut 204 and contain a slot 208 which receives a pin element 210 of the nut 204. An adapter 212 is located on the shaft 202 to attach the nut 204 to the plate housing 206. A release plate 214 is downwardly biased (i.e. by gravity, spring, or other device) and slideably received within a vertical plate slot 216 formed in the plate housing 206. An engagement portion 218 is formed as a hole in the release plate 214 for normally coupling and slideably engaging the release plate 214 to an annular groove 215 on the nut adapter 212.

In an emergency, the release plate 214 can be manually uncoupled or disengaged from the nut adapter 212, thus disengaging the actuator 198 from the front carriage assembly 74. A release aperture 220 is formed as a hole in the release plate 214 and is positioned below but connected to the engagement portion 218. The release aperture 220 has a greater diameter than the engagement portion 218. Preferably the release aperture 220 and the engagement portion 218 partially overlap, with the engagement portion 218 having a diameter slightly larger than the groove 215 and the release aperture 220 having a clearance diameter significantly larger than the nut adapter 212 adjacent to the groove 215. As the release plate 214 is raised, the engagement portion 218 is raised out of the groove 215 in the nut adapter 212 and the release aperture 220 allows the release plate 214 to be slid over the nut adapter 212, thereby uncoupling or disengaging the plate housing 206 and front carriage assembly 74 from the actuator 198.

An emergency release element 222 is provided for raising the release plate 214 and disengaging the plate housing 206 from the actuator 198. The emergency release element 222 has a finger switch 224 allowing a user to manually pull forward the spring biased emergency release element 222. The emergency release element 222 allows a user to manually remove cassette 50 from the pump 10 in cases of pump malfunction or loss of power.

Figure 17:
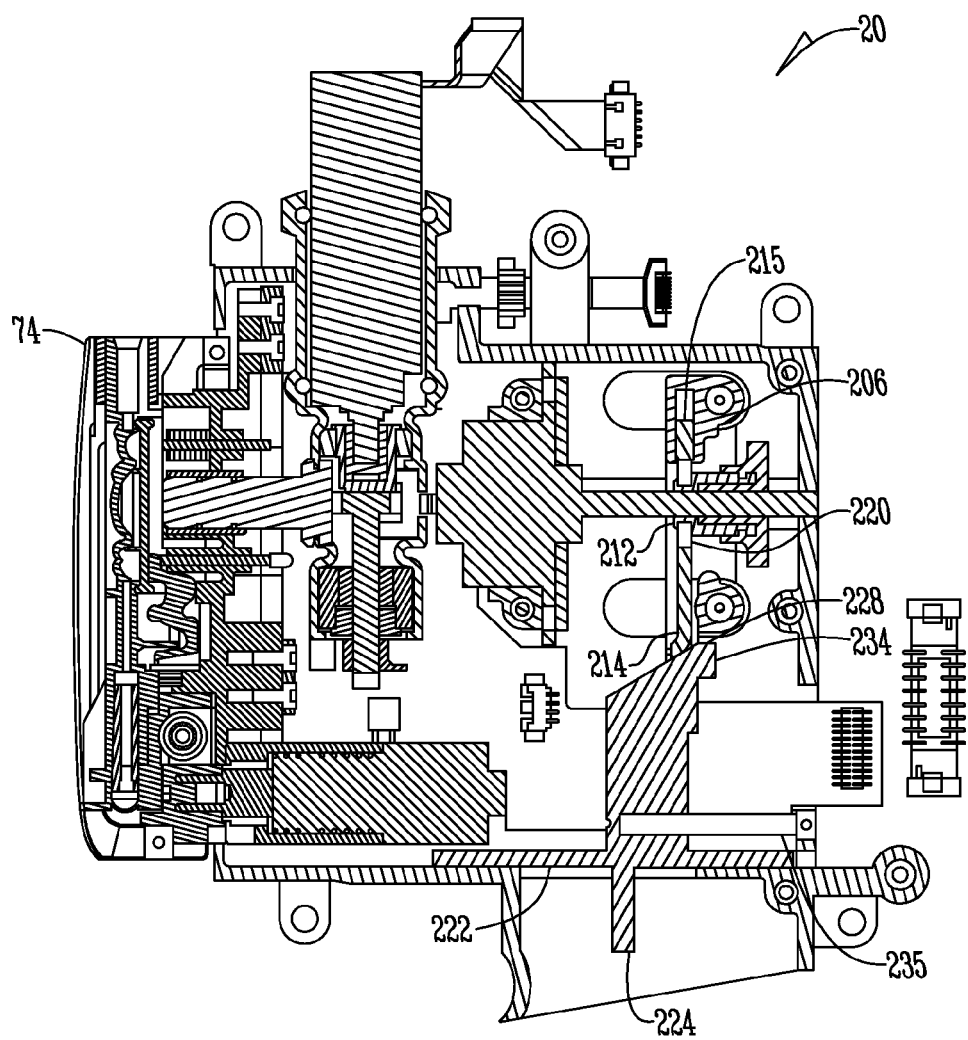
FIG. 17 is a vertical cross sectional side view of a prior art loader having the emergency released engaged with the actuator assembly so that the release plate is raised.

With reference to FIGS. 14 and 17, as the emergency release element 222 moves forward, a vertical column 226 having an upper end forming a ramp 228 engages a bottom edge 230 of the release plate 214. The vertical column 226 passes between lower legs 232 of the plate housing 206, with the ramp 228 gradually raising the release plate 214 until the release aperture 220 is positioned around or aligned with the nut adapter 212. At the apex of the ramp 228, side tabs 234 extending horizontally from the vertical column 226 engage the lower legs of the plate housing 206.

Figure 18:
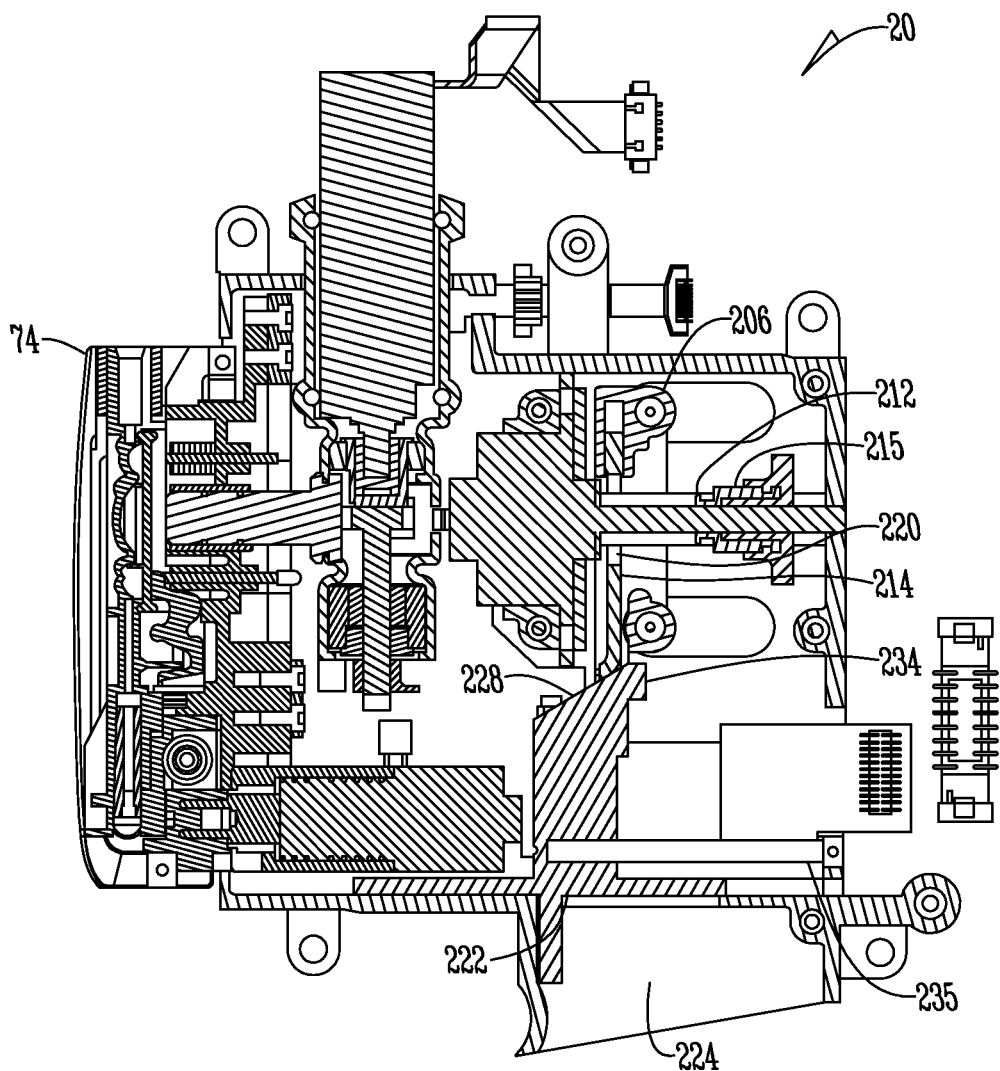
FIG. 18 is a vertical cross sectional side view of the loader where the actuator assembly is disengaged.

With reference to FIG. 18, once the release plate 214 is raised, the forward motion of the emergency release element 222 causes the side tabs 234 to push the plate housing 206 forward. The release aperture 220 is slid over the nut adapter 212, and the plate housing 206 and front carriage assembly 74 are moved to the open position disengaged from the actuator 198.

With reference to FIGS. 16, 17 and 18, once the user activates the emergency release element 222, it can then be released. A spring 235 (or other biasing device) biases or returns the emergency release element 222 to its normal position, while the plate housing 206 and front carriage assembly 74 remain in the open position and also remain disengaged from the actuator 198. The spring biased release plate 214 lowers itself to rest on the shaft 202. In this position, the release plate 214 cannot be reengaged to the nut adapter 212.

Further, manually pressing the front carriage assembly 74 to a closed position while pulling the emergency release element 222 forward will not reengage the nut adapter 212 as a certain amount of tension between the nut adapter 212 and release plate 214 was released when the emergency release element 222 was originally pulled. This amount of released tension is enough to prevent a user from manually forcing the front carriage assembly 74 back far enough to register the engagement portion 218 of release plate 214 with the groove 215 in the nut adapter 212.

When the actuator 198 originally drove the front carriage assembly 74 to a closed position, the actuator 198 induced the above-mentioned releasable tension by pulling the main carriage 78 hard against the posts 182. The actuator 198 is driven past the point of initial contact until increasing mechanical resistance stalls it or a predetermined electrical load is reached. The nut 204 and nut adapter 212 are driven back as far as possible. In doing so, all of the dimensional slack is taken out of the interconnected chain of components, including but not limited to the main chassis 122, side chassis 236, 238, rear carriage assembly 190 (actuator 198, shaft 202 and nut 204), side plates 196, and main carriage 78. These components are placed under tension or compression, depending on their function, by the pull of the overdriven actuator 198. The user who tries to reengage the nut adapter 212 and release plate 214 would have to manually recreate these conditions in order to reengage. However, the user cannot reach the internal components such as the actuator 198, threaded shaft 202 and nut 204 to establish such conditions.

The prevention of manual reengagement between the nut adapter 212 and release plate 214 provides a continuous visual indicator that the pump 10 is not operational due to the open position of front carriage assembly 74. The prevention of manual reengagement between the adapter 212 and release plate 214 also ensures that error signals generated by pump 10 must be addressed prior to recoupling or reengaging the nut adapter 212 and release plate 214 and restarting the pump 10.

Thus, it can be appreciated that no manual closure of the front carriage assembly 74 is possible with the present invention. By pump 10 requiring the automated closure of front carriage assembly 74, a user is not able to insert a cassette 50 into a non-operational pump 10. This ensures that the full array of detection and safety elements in pump 10 are active when a cassette 50 is engaged with the pump 10.

To reengage the actuator 198 the user must electrically drive the actuator 198 forward while simultaneously pulling the emergency release element 222 forward. This allows the groove 215 of the nut adapter 212 to be driven underneath the engagement portion 218 of the release element 214. Once the groove 215 of the nut adapter 212 is beneath the engagement portion 218, the emergency release element 222 can be released. When the emergency release element 222 is released, the engagement portion 218 drops into the groove 215 of the nut adapter 212 and reengages the front carriage 74 to the actuator 198.

Figure 15:
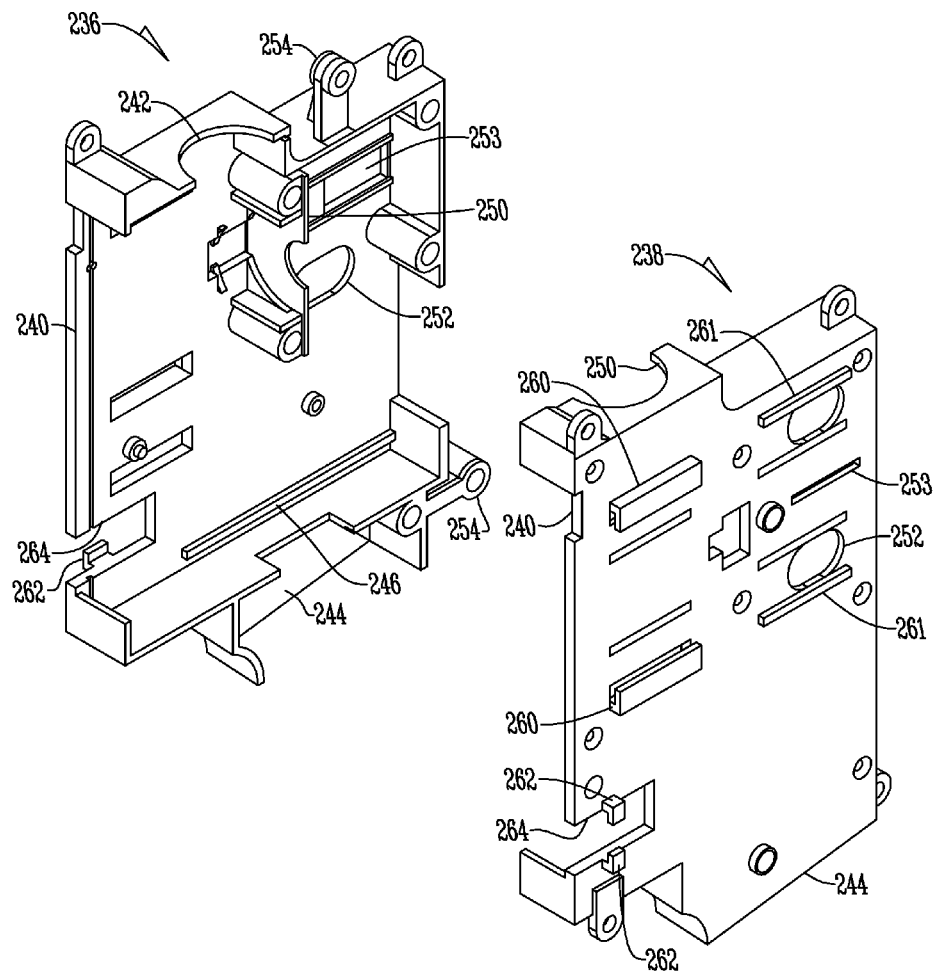
FIG. 15 is an exploded perspective right side view of the left and right chassis substrate.

With reference to FIG. 15, left and right side chassis 236 and 238 house the pump chassis assembly 120 of FIG. 9 and the rear carriage assembly 190 of FIG. 14. A front opening 240 is formed in the side chassis 236 and 238 to fit around the main chassis 122. An upper opening 242 is formed in the side chassis 236 and 238 to fit around the motor 142.

A lower channel 244 is formed in the side chassis 236 and 238 to fit around the manual release finger switch 224. The lower channel 244 surrounds the finger switch 224 and is sealed to the manual release opening 26 of infuser cover 16, allowing a user to access the finger switch 224 from outside the infuser cover 16. A manual release groove 246 slideably receives a horizontally flat plate slider 248 of the emergency release element 222, allowing the emergency release element 222 to slide back and forth along the manual release groove 246.

An actuator seat 250 is formed in the side chassis 236 and 238 to fit around the actuator 198 and secure the actuator to the side chassis 236 and 238. Rear carriage ports 252 are formed in the side chassis 236 and 238 to allow the rear carriage fasteners 192 to pass through the side chassis 236 and 238 to attach the rear carriage assembly 190 to the side plates 196 of the front carriage assembly 74. The rear carriage ports 252 also allow the rear carriage fasteners 192 to move back and forth as the actuator 198 drives the plate housing 206. Nut ports 253 slideably receive the pin elements 210 of the nut 204 and prevent the nut 204 from rotating when actuator 198 is activated.

With reference to FIGS. 6, 14 and 15, female fasteners 254 extend from the outer surface of side chassis 236 and 238 to secure an infuser circuit board 256 via male fasteners 258.

With reference to FIGS. 6, 9 and 15, side plate channels 260 are formed as paired "L" shaped brackets on the outer surface of side chassis 236 and 238. The side plate channels 260 slideably hold the side plates 196 of the front carriage assembly 74 as it moves back and forth. Additionally, side plate guides 261 are formed as paired box shaped bumpers adjacent the rear carriage ports 252 on the outer surface of side chassis 236 and 238. The side plate guides 261 are spaced apart and may be preferably positioned parallel to one another. The side plate guides 261 are positioned on both the top and bottom of the side plates 196 to prevent rotation of the side plates 196 near the rear carriage ports 252. These side plate channels 260 and side plate guides 261 provide for a straight line insertion of the front carriage assembly 74, which avoids the adverse rotational effects of prior art manual loaders.

Air cam channels 262 formed as paired "L" shaped brackets on the outer surface of side chassis 236 and 238. The air cam channels 262 slideably hold the air cam plates 154 of the front carriage assembly 74 as it moves back and forth horizontally. Air cam ports 264 are formed through the side chassis 236 and 238 adjacent the air cam channels 262. The air cam ports 264 permit the cam elements 150 of the air sensors 144 to contact the air cam plates 154.

With reference to FIGS. 6 and 8, a position sensor 266 is attached to the outer surface of the left side chassis 236. The position sensor 266 monitors the position of a slot 268 formed in a position plate 270. The position plate 270 is preferably an integral portion of the left side plate and extends horizontally from the left front fascia 102. Alternatively, the position sensor 266 can monitor the position of an end edge 272 of the position plate 270. By monitoring the position of the position plate 270 the position sensor 266 detects the overall position of the front carriage assembly 74 and the main carriage 78. The position sensor 266 shown is a linear pixel array sensor that continuously tracks the position of the slot 268, and does not merely indicate when the slot 268 has passed a fixed point. It will be understood that other devices can be used for the position sensor 266, such as an opto-tachometer sensor.

Figure 21:
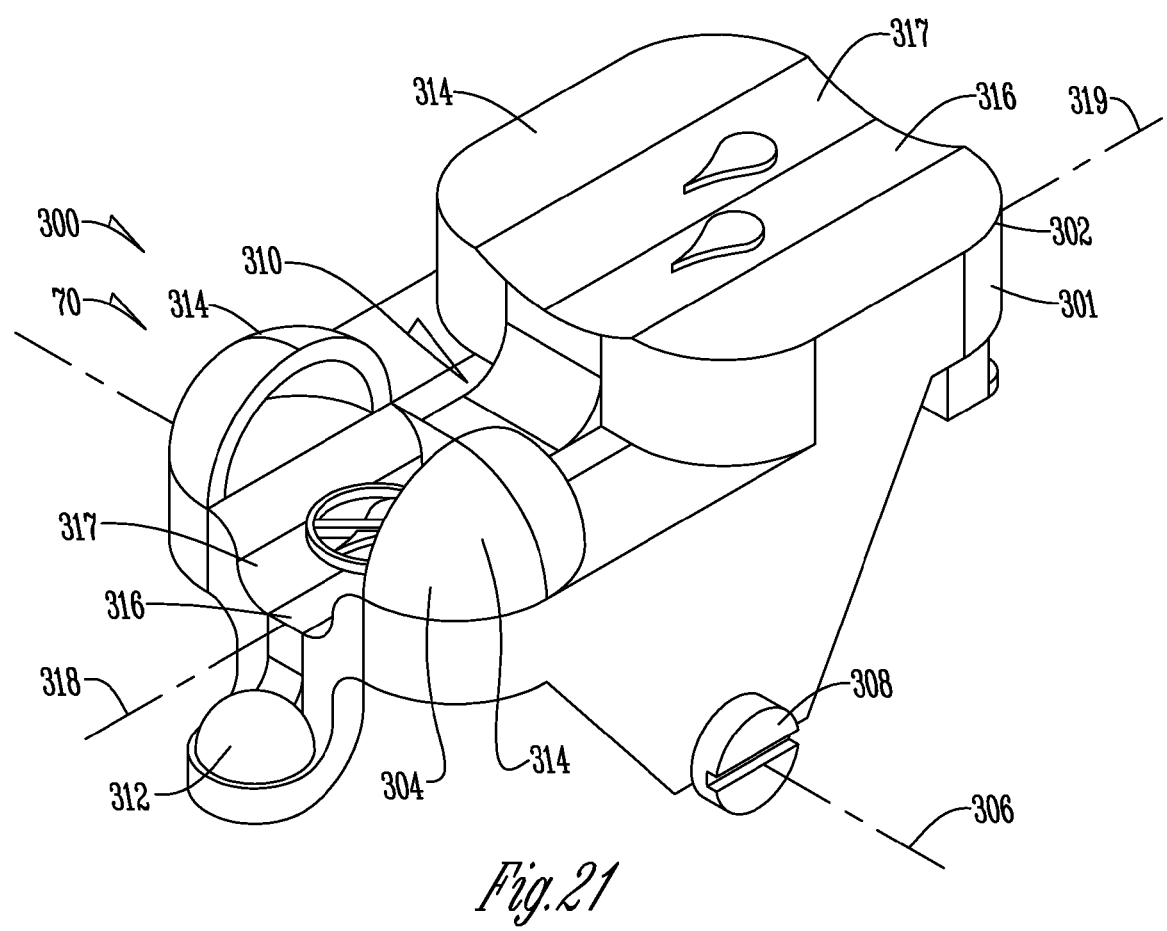
FIG. 21 is a perspective view of a flow stop according to the present invention.
Figure 22:
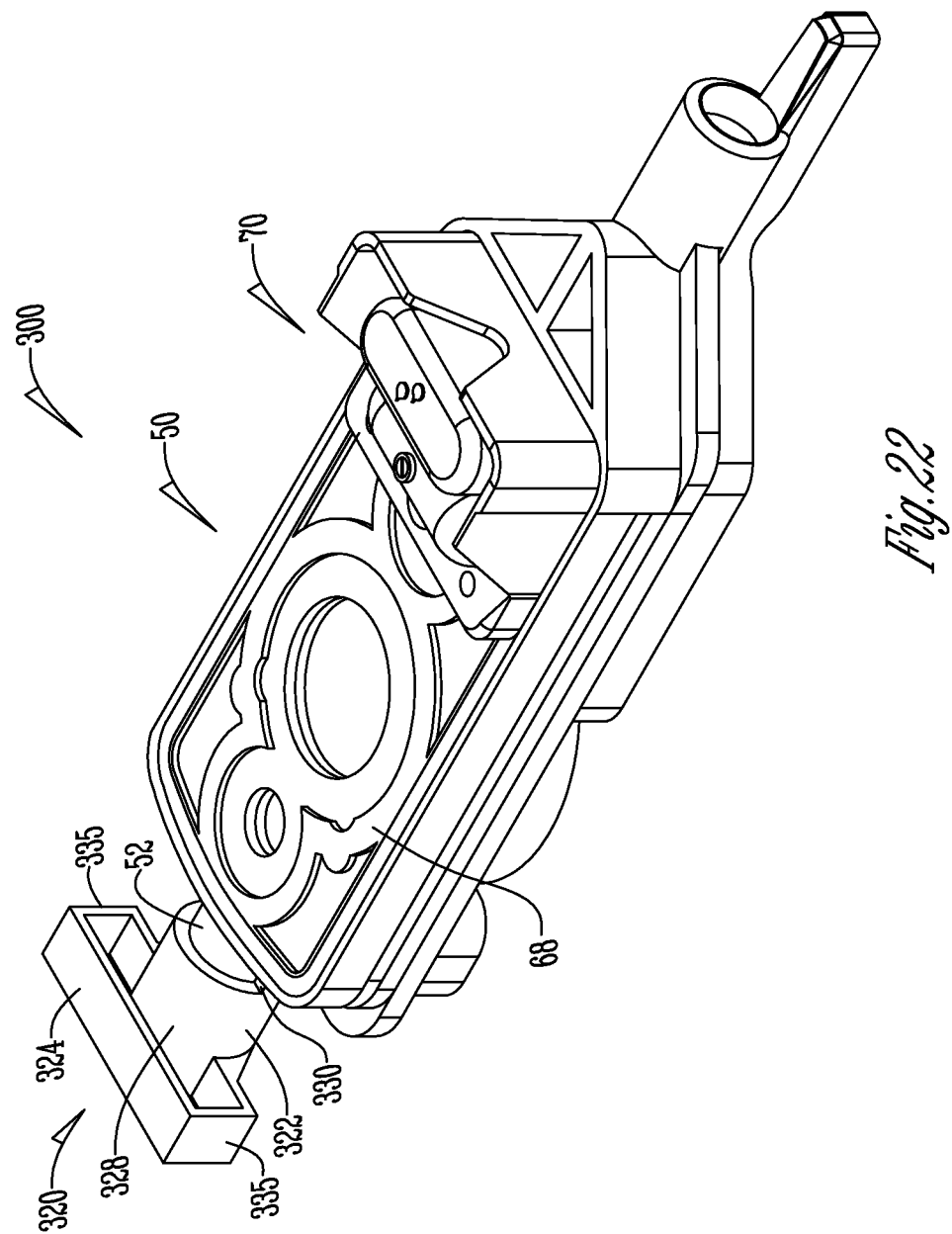
FIG. 22 is a perspective view of a cassette with a collar according to the present invention.
Figure 23:
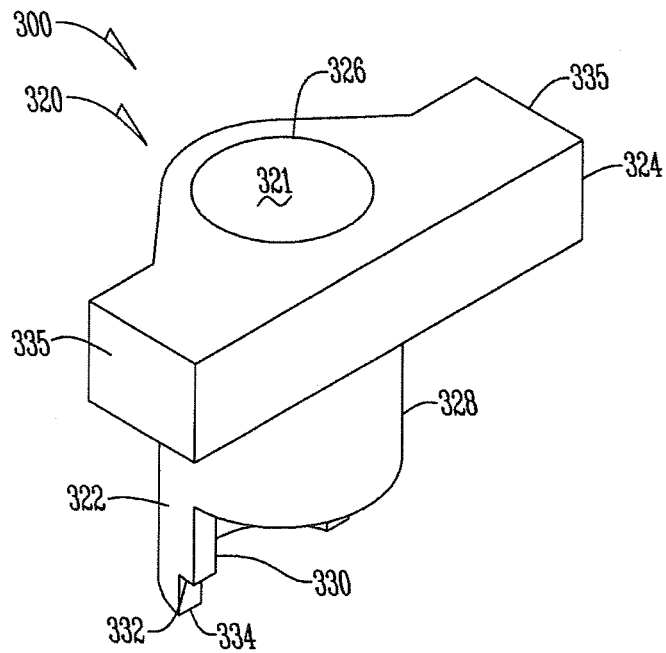
FIG. 23 is a top perspective view of a collar according to the present invention.
Figure 24:
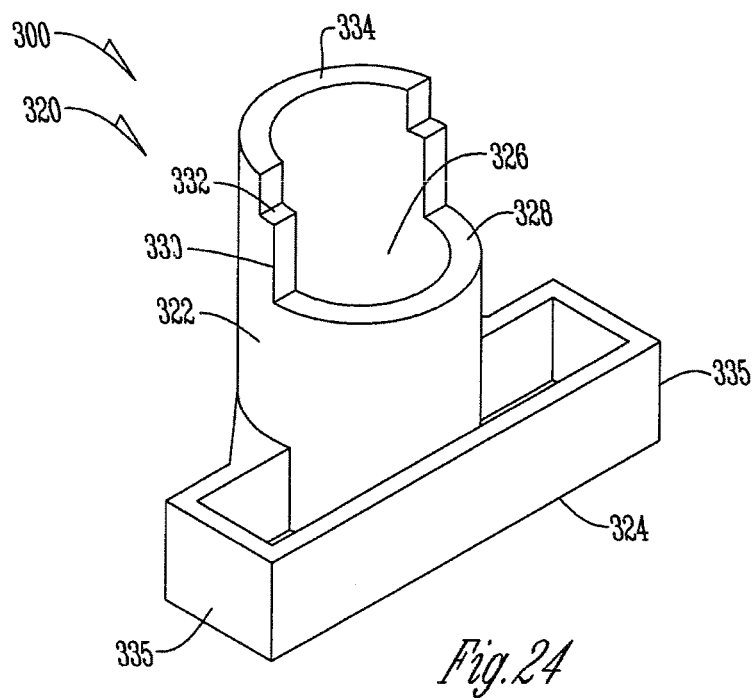
FIG. 24 is a bottom perspective view of a collar according to the present invention.
Figure 25:
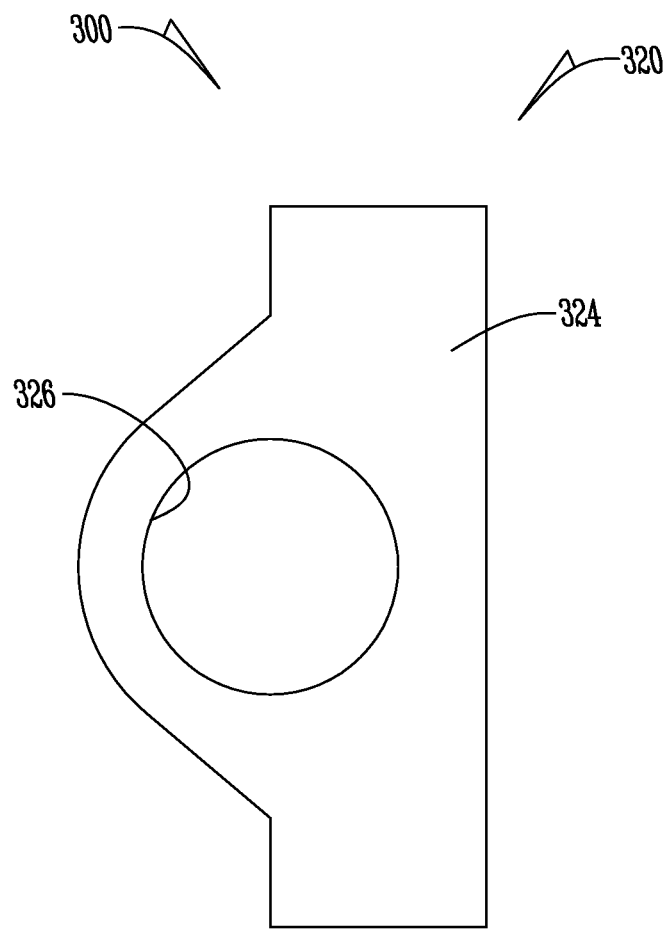
FIG. 25 is a top plan view of the collar of the present invention.

FIGS. 21-36 show preventing means 300 that prevent contact of the flow stop 70 with components of the medical pump 10 during removal of the cassette 50. In a first embodiment shown in FIG. 21 the preventing means 300 is an improved flow stop 70 where the flow stop 70 is made of one piece construction with a main body 301 having a raised first section 302 and a raised second section 304 that are spaced apart on either side of a pivot axis 306. The flow stop 300 pivots about the pivot axis 306. A pivot element 308 on the flow stop 70 is operatively connected to and interacts with a mating pivot element 309 (see FIG. 5) on the main body 56 of the cassette 50. By way of example and not limitation, the pivot element 308 on the flow stop is illustrated as one or more pivot pins protruding from the flow stop 70. The pivot element 308 is pivotally connected to the cassette main body 56 via a hole or slot. However, one skilled in the art will appreciate from this description that the pivot element 308 on the flow stop 70 could be a hole or slot and a mating pin or pins could be provided on the cassette main body 56.

A rib 310 is connected to and separates the first and second sections 302 and 304. As best understood in view of FIGS. 20 and 21, extending from the second section 304 is a pressure sensing element 312 that when in its normally closed or lowered position engages the outlet membrane or diaphragm 64 of the cassette 50 downstream of the outlet valve and senses fluid pressure at the outlet of the cassette 50. As described above, the flow stop 70 prevents unrestricted or uncontrolled fluid flow through the cassette.

Each of the first and second sections 302 and 304 have opposing upright side walls 314 with a groove 316 formed on a top wall 317 that extends between the side walls 314. Preferably the groove 316 is arcuate in shape extending downwardly and inwardly from each of the side walls 314 to form each groove 316. Specifically, the main body 301 has a central longitudinal axis 318 and the groove 316 has a central longitudinal axis 319 that is aligned with the central longitudinal axis 318 of the main body 301.

Thus material is removed from the first and second sections 302 and 304 of the flow stop 70 as compared to prior art flow stops. As a result, when the cassette 50 is removed, because of the grooves 316 in the first and second sections 302 and 304, less material is presented or protruding that can inadvertently contact components of the medical pump 10. For example, the components of concern in the particular medical pump shown are the distal pin 143 and the plunger 136. Thus the grooves 316 prevent inadvertent actuation of the flow stop 70 during installation or removal of the cassette 50.

Figure 26:
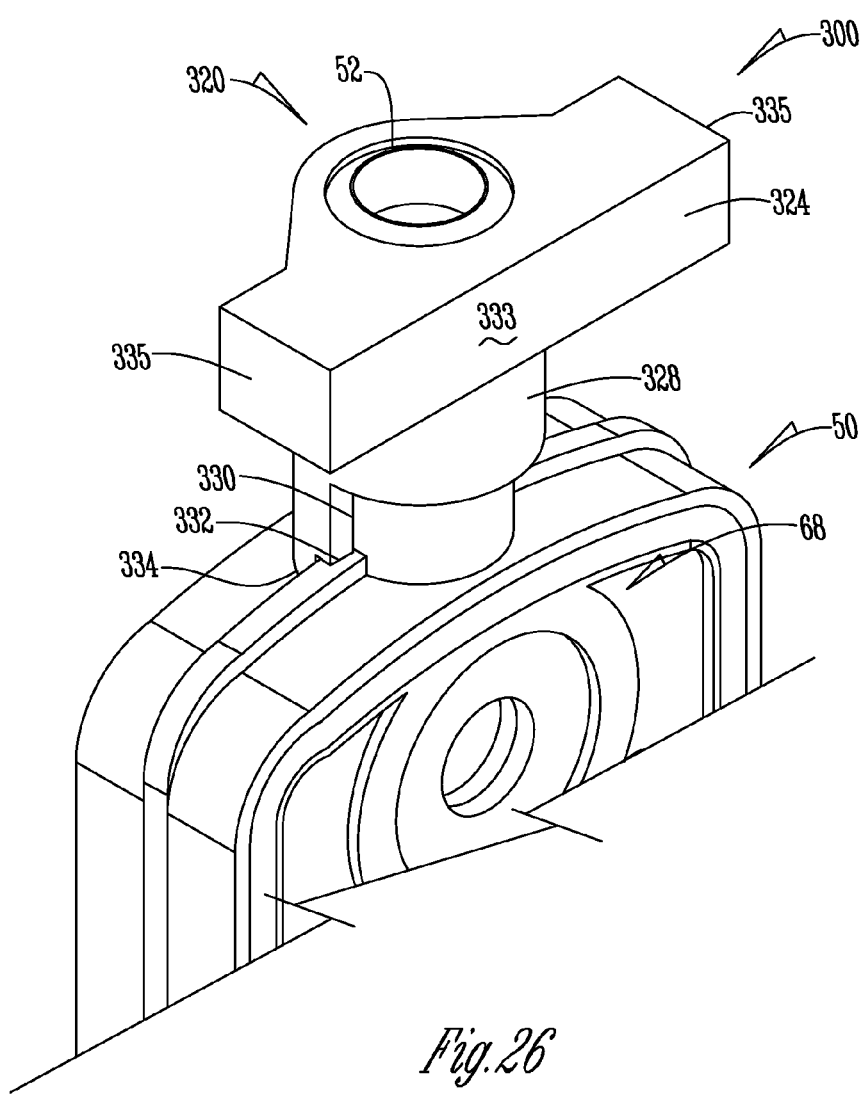
FIG. 26 is a side perspective view of a collar on a cassette according to the present invention.
Figure 27:
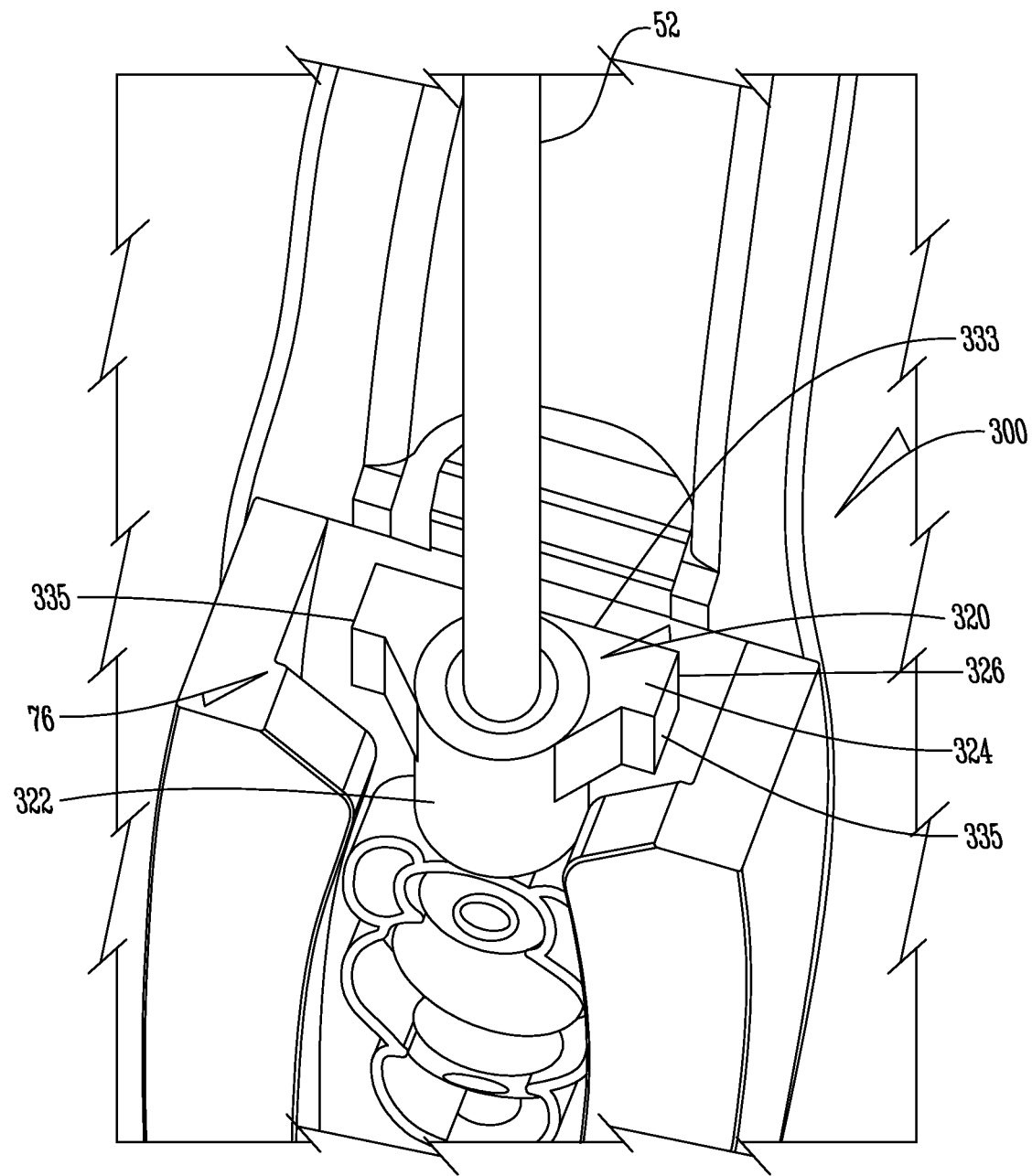
FIG. 27 is a top perspective view of a cassette with a collar of the present invention in a fully open loader.
Figure 28:
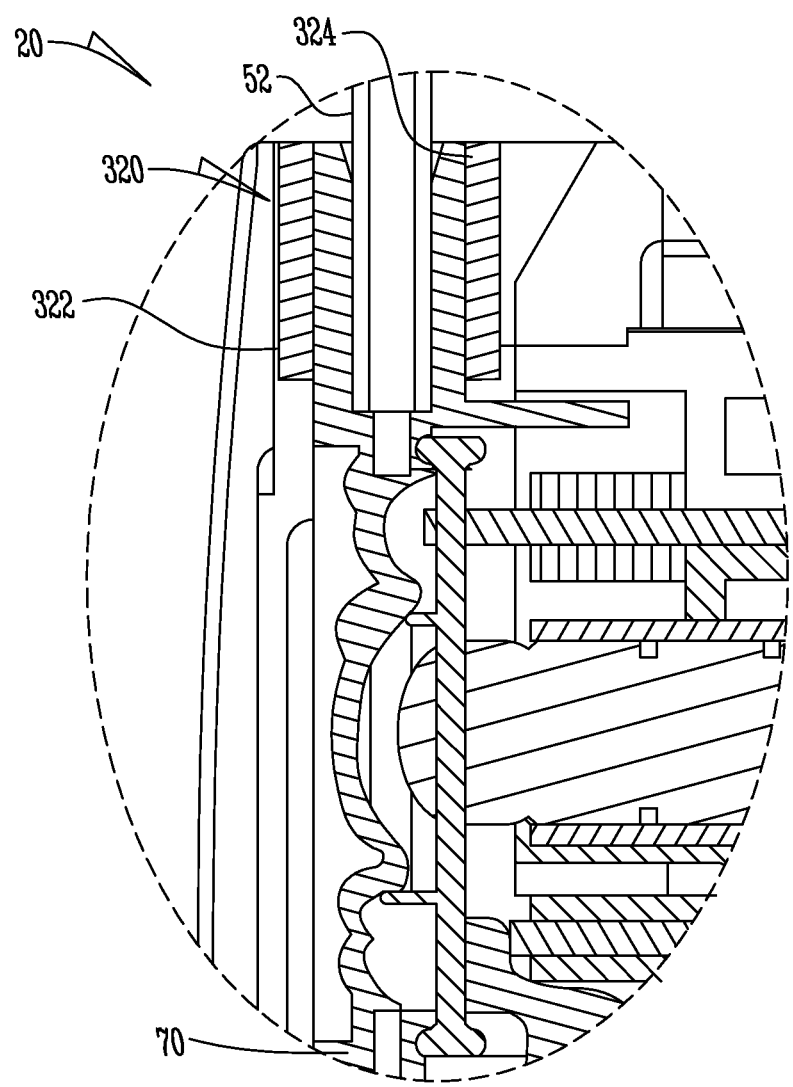
FIG. 28 is a sectional view of a closed loader with a cassette inserted having a collar of the present invention.
Figure 29:
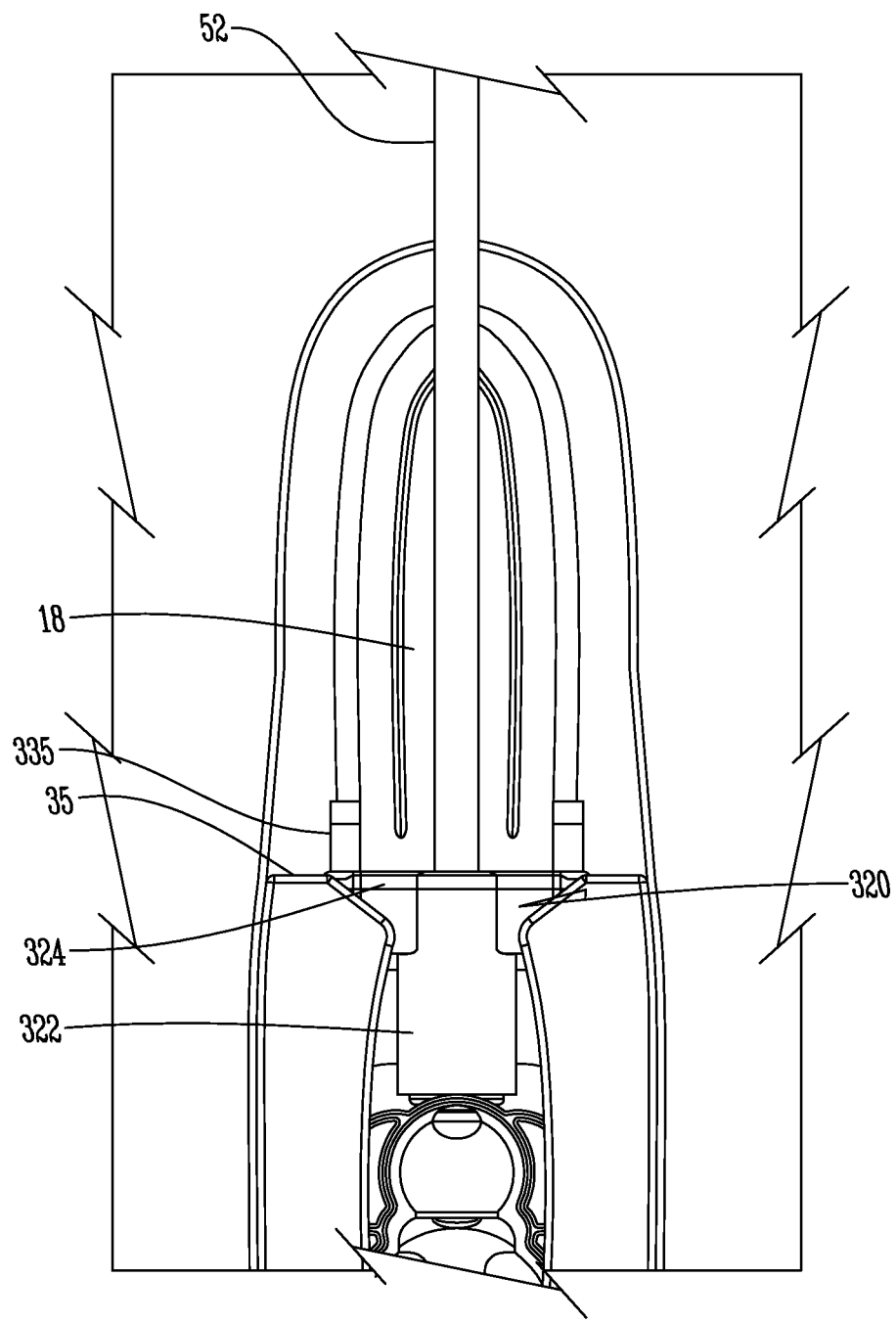
FIG. 29 is a side perspective view of a cassette loader having a collar engaging the indicator window of the pump.

In an alternative embodiment shown in FIGS. 22-29 the preventing means 300 is a collar element 320 that surrounds and is secured to the inlet 52 of the cassette 50. The collar element 320 can additionally or alternatively be secured to the inlet 52 by being secured to the main body 56 of the cassette 50, as described below. The collar element 320 is generally T-shaped having a base leg 322 that is circular in cross section and a cross member 324 connected to and extending from the base leg 322. The base leg 322 of the collar 320 has an opening 326 disposed therein that surrounds the inlet 52 of the cassette 50 such that the collar element 320 is slideably and removably disposed or otherwise received around the inlet 52. In other words, the base leg 322 of the collar 320 has a hollow interior with a sidewall 321 that defines the opening 326. Extending from the cross member 324 the main body 328 of the base leg 322 has a first arcuate flange 330 that extends partially around the main body 328 to form a lip element 332 with a second arcuate flange 334 that has an angular span that is less than the angular span of the first arcuate flange 330. In this way the lip element 332 and first arcuate flange 330 engage a perimeter of the cassette, as best shown in FIG. 26, thus accommodating the structure of the cassette 50. In this manner the collar 320 can be secured to an existing or previously manufactured cassette 50. The collar element 320 can be secured against rotational and longitudinal movement with respect to the inlet 52 and cassette 50 by using adhesives, heat sealing or other known securing means in a well known manner at any of the interfaces 52, 321; 50, 330, 332, 334, 321. In another embodiment the collar element 320 can be integrally molded or formed as a single unitary piece with the inlet 52 of the cassette 50.

As best shown in FIGS. 26-29 the cross member 324 angles away from the base leg 322 and extends laterally such that the width of the cross member 324 is greater than the diameter of the base leg 322. The cross member 324 is generally rectangular in cross section having parallel end faces 335 that run parallel to sidewalls of the loader 20. The front face 333 of the cross member 324 has a height approximately equal to the height of the inner surface 68 of the cassette 50. Thus, the front face 333 is substantially co-planar with the surface 68 of the cassette 50. The cross member 324 also is approximately as long as the cassette 50 is wide such that the cross member 324 engages a part of the pump 10 when the loader 20 is not in a fully open position.

In one embodiment shown in FIGS. 30-33 the inlet 52 further has a protrusion 337 or key extending from an exterior surface of the inlet 52 that matingly corresponds to a retention notch 331 in the base leg 322 of the collar element 320A to provide a locking connection that prevents longitudinal movement of the collar 320. In another embodiment the collar element 320A can be integrally molded or formed as a single unitary piece with the inlet 52 of the cassette 50.

Figure 31:
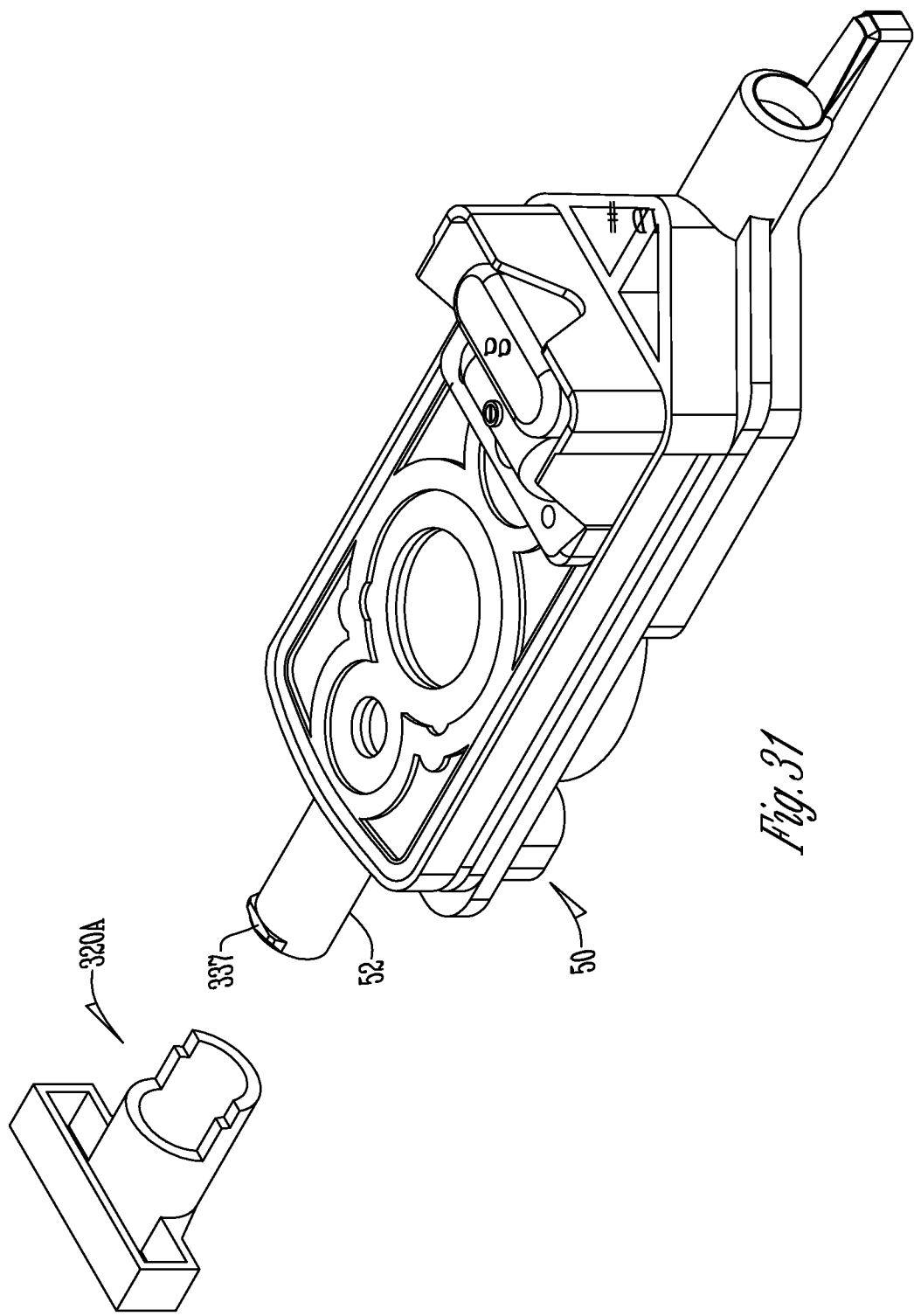
FIG. 31 is perspective view of a cassette and collar of the present invention.
Figure 32:
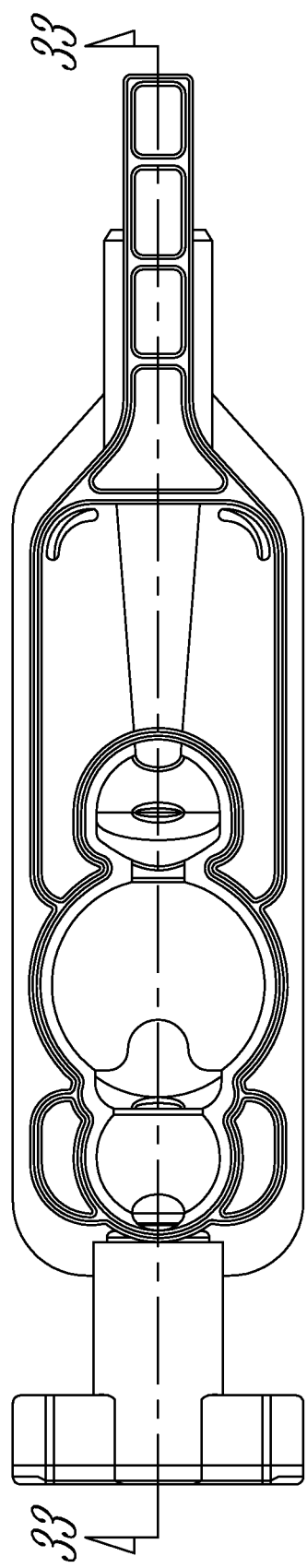
FIG. 32 is a plan view of a cassette and collar of the present invention.
Figure 33:
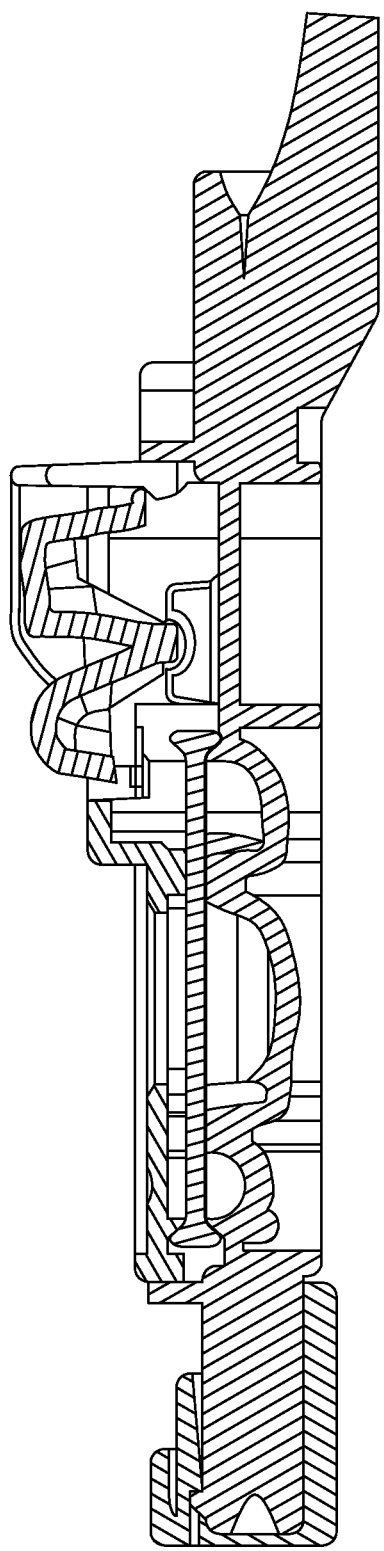
FIG. 33 is a sectional view of a cassette and collar of the present invention taken from FIG. 32 along line 33-33.

FIGS. 31-33 show shows further detail regarding the alternative embodiment of the preventing means 300 that utilizes a collar element 320A that surrounds and is snappingly secured to the inlet 52 of the cassette 50 via a mating protrusion and retention notch arrangement. The collar element 320A is generally T-shaped having a base leg 322A that is circular in cross section and a cross member 324A connected to and extending from the base leg 322A. The base leg 322A of the collar 320A has an opening 326A disposed therein that surrounds the inlet 52 of the cassette 50 such that the collar element 320A is disposed around the inlet 52. In other words, the base leg 322A of the collar 320A has a hollow interior with a sidewall 321A that defines the opening 326A. In other words, the opening 326A is adapted to receive the inlet 52 with the protrusion 337 thereon. In the example shown, the inlet 52 is slideable along a longitudinal axis of the opening 326 for assembly purposes.

A retention notch 331A is formed in the sidewall 321A adjacent the opening 326A in the base leg of the collar element 320A and receives and engages the protrusion 337 so to retain the collar element 320A on the inlet 52. The opening 326A of the collar element 320A is tapered and narrows toward the retention notch 331A. The retention notch 331A defines a ledge that is perpendicular to a longitudinal axis of the opening so as to inhibit longitudinal movement of the collar element 320A with respect to the inlet 52 in at least one direction.

Figure 30:
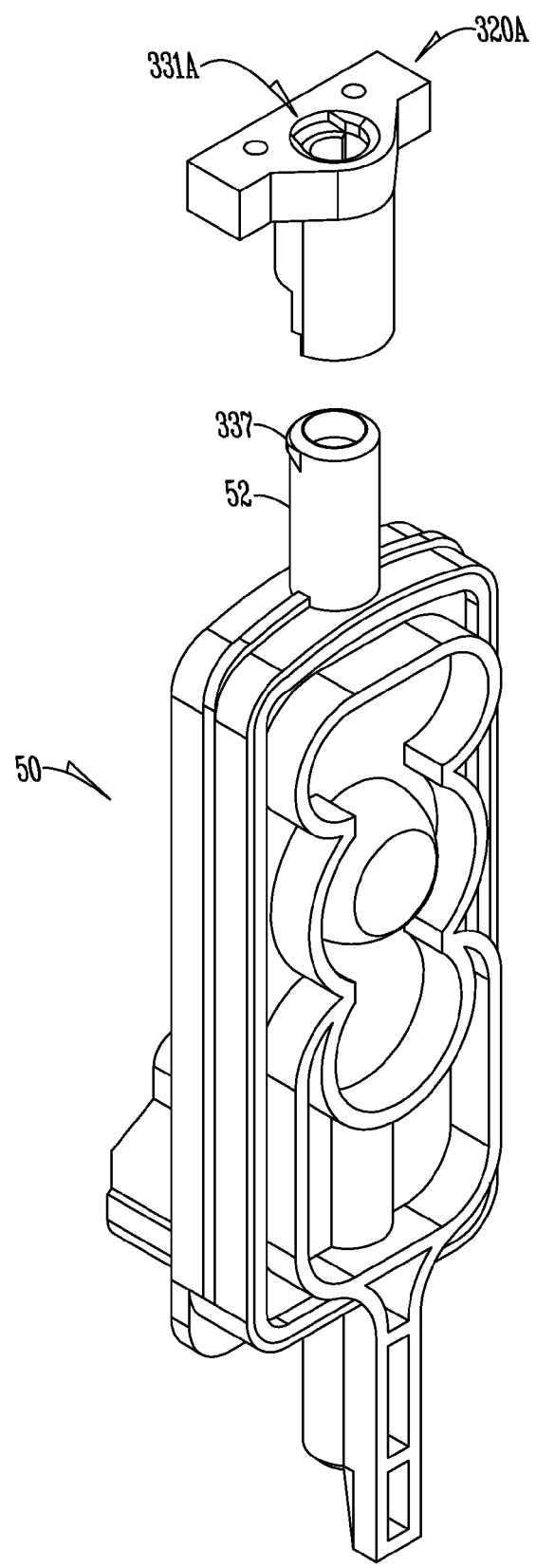
FIG. 30 is an exploded perspective view of a cassette and collar of the present invention.
Figure 30B:
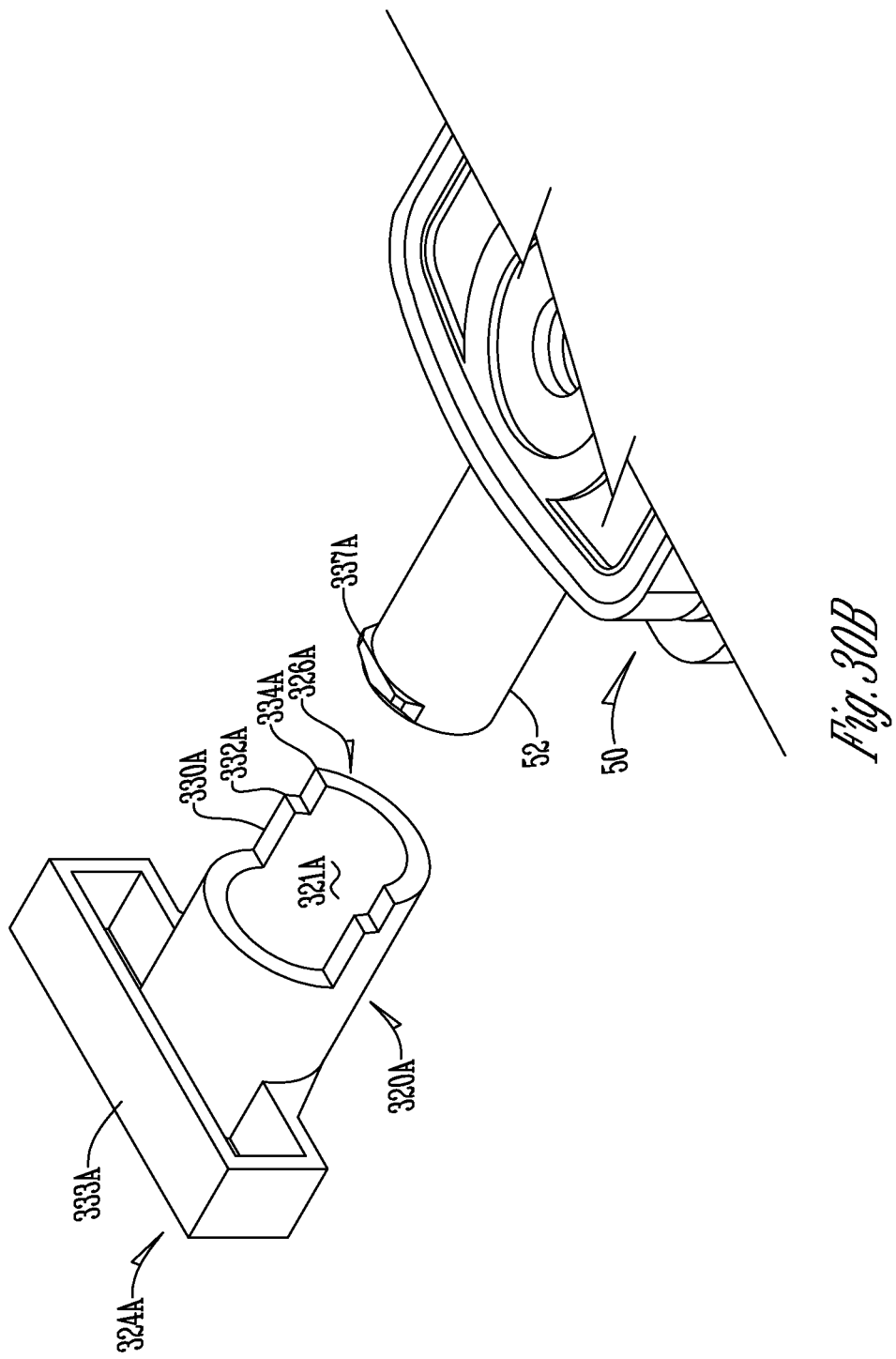
FIG. 30B is an enlarged exploded perspective view of a portion of a cassette and collar of the present invention wherein the components have been rotated to better show an optional protrusion on the cassette for retaining the collar.
Figure 30C:
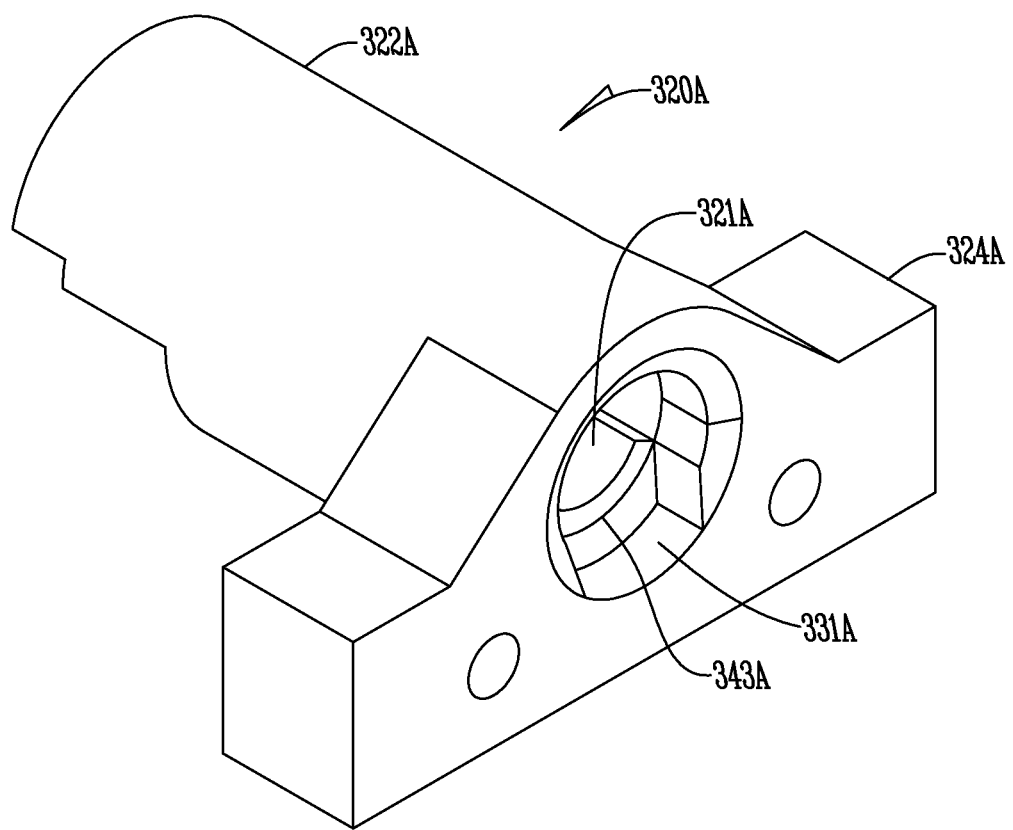
FIG. 30C is an enlarged perspective view of a collar of the present invention.
Figure 30D:
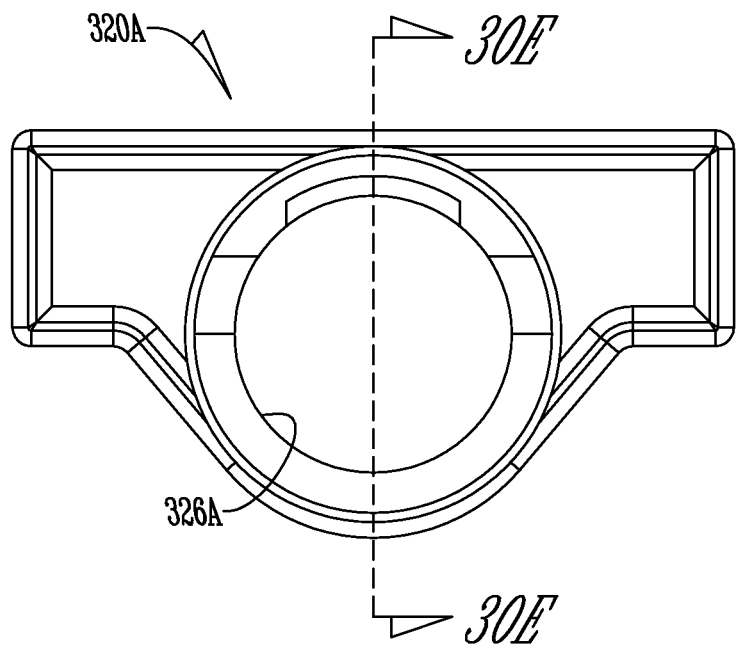
FIG. 30D is a bottom plan view of a collar of the present invention.
Figure 30E:
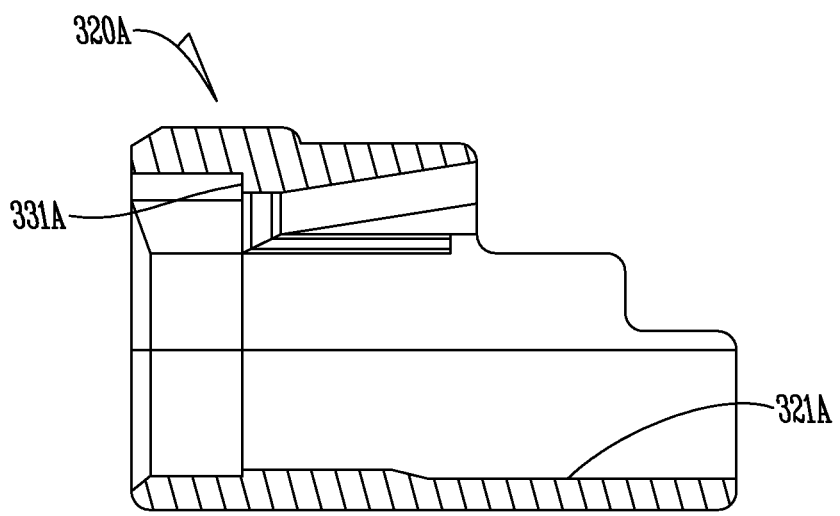
FIG. 30E is a sectional view of the collar taken from FIG. 30D along line 30E-30E.
Figure 30F:
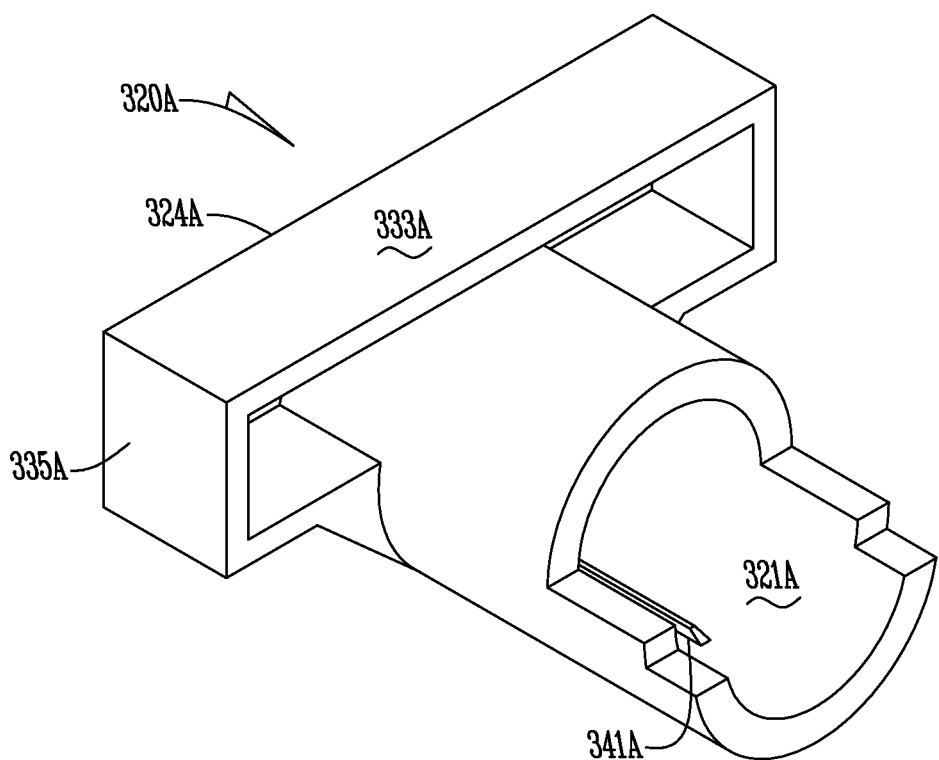
FIG. 30F is a bottom perspective view of a collar of the present invention that is equipped with one or more optional guide ribs.

The opening 326A of the collar element 320A can optionally be tapered or ramped, as best seen in FIGS. 30D and 30E, so that it narrows toward the retention notch 331A. As exemplified in FIG. 30F, one or more radially spaced elongated ribs 341A optionally can be provided extending from the sidewall 321A and extending longitudinally to help guide, reduce crushing stresses and accommodate tolerance variations between the mating parts. A raised ramp or lead-in lip element 343A can extend from the sidewall 321A into the opening 326A of the collar element 320A at a location adjacent to the retention notch 331A so that an external force must be applied to force the protrusion 337 on the inlet 52 over the lip element to reach the retention notch 331A and "snap" in place.

In other words, FIGS. 30-33 show an embodiment where a protrusion 337 is provided. In this embodiment the protrusion 337 is formed on the inlet 52. As best shown in FIGS. 30D, 30E and 33 a tapered sidewall 352A that tapers from a first end 354A to a second 356A and terminates in a lip element 358A. In this manner once the protrusion 337 is forcibly pushed past the lip element 358A it can reach the retention notch 331A. Once the protrusion 337 reaches the notch 331A, the ledge 345A of the notch 331A tenaciously and physically engages the protrusion 337 to prevent movement of the collar 320A off of the inlet 52. In this manner not only does the collar 320A attach to the inlet but additionally the collar 320A is secured or locked onto the inlet 52 and inhibited against axial movement in at least one direction. One skilled in the art will appreciate that the protrusion could be formed on the inside diameter of the opening of the collar element and the notch formed on the inlet and other mating structures reversed accordingly to provide yet another embodiment of a preventing means 300 that utilizes a collar element that surrounds and is snappingly secured to the inlet of the cassette via a mating protrusion and retention notch arrangement.

However, referring again to an embodiment as shown in FIGS. 30-33, extending from the cross member 324A the main body 328A of the base leg 322A has a first arcuate flange 330A that extends partially around the main body 328A to form a lip element 332A with a second arcuate flange 334A that has an angular span that is less than the angular span of the first arcuate flange 330A. In this way the lip element 332A and the first arcuate flange 330A engage a perimeter of a cassette, as best shown in FIG. 26 thus accommodating the structure of the cassette 50. In this manner the collar 320A can be secured to an existing or previously manufactured cassette 50. The collar element 320A can be secured against rotational and longitudinal movement with respect to the inlet 52 and cassette 50 by using adhesives, heat sealing or other known securing means in a well known manner at any of the interfaces 52, 321A; 50, 330A, 332A, 334A, 321A. In another embodiment the collar element 320A can be integrally molded or formed as a single unitary piece with the inlet 52 of the cassette 50.

The cross member 324A angles away from the base leg 322A and extends laterally such that the width of the cross member 324A is greater than the diameter of the base leg 322A. The cross member is generally rectangular and cross section having parallel end faces 335A that run parallel to the sidewalls of the loaders 20. The front face 333A of the cross member 324A has a height approximately equal to the height of the inner surface 68 of the cassette 50. Thus the front face 333A is substantially co-planar with the surface 68 of the cassette 50. The cross member 324A also is approximately as long as cassette 50 is wide such that the cross member 324A engages a part of the pump 10 when the loader 20 is not in a full open position.

The pump 10 has an indicator window 18 that has a window body 30 and the collar element 320A engages the indicator window 18 when a user attempts to prematurely remove the cassette 50 from the medical pump, i.e., before the loader 20 is in a fully open position. Thus, the width, length and shape of the collar element 320A generally register with or match with some clearance with the loader top opening 76. Consequently, the dimensions of the collar 320A are slightly less than those of the opening 76 exposed or created when the cassette loader 20 is fully open. Yet, the dimensions are such that the cross member 324A hits the bottom edge of the indicator window 18 when the loader door is closed and partially closed, thus preventing a user from prematurely pulling out or withdrawing a cassette 50. As a result, the size and shape of the collar 320A also prevent the flow stop 70 from contacting the top finger element 166 of the fixed seat 162 (see FIGS. 9 and 11) or other components of the pump 10 when a user pulls the cassette 50 upwardly or longitudinally out of the loader 20.

When the cassette loader 20 goes from a fully closed to a fully opened position, if the loader 20 is not in the fully opened position the cross member 324A of the collar 320 engages the pump at the bottom edge along the front of the indicator window 18, thereby preventing the cassette 50 from being removed until the loader 20 is in a fully open position. Therefore, by preventing the cassette 50 from being removed before the loader 20 is in the fully open position the flow stop 70 is prevented from engaging components of the pump 10 and causing free flow inadvertently.

FIGS. 34-39 show yet another embodiment of the preventing means 300 where the preventing means 300 prevents the cassette 50 from being removed from the cassette loader 20 until the loader 20 is in a fully opened position. In this embodiment the cassette 50 has a flange 336 secured adjacent inlet 52 and extending outwardly from the inner face 68 of the cassette 50. The flange 336 can be bonded to the cassette 50, molded with the cassette body, or attached in any way known in the art.

Figure 39:
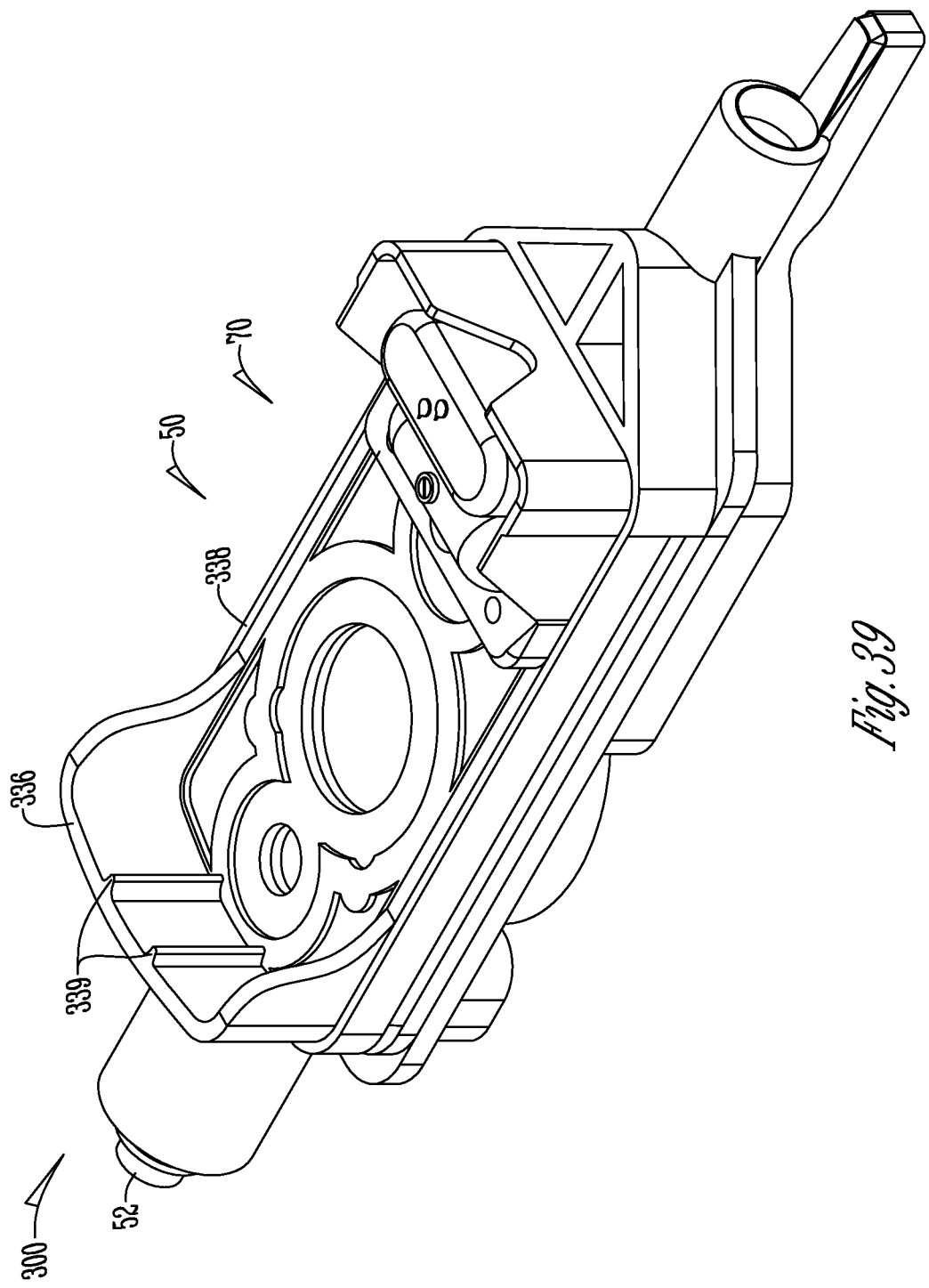
FIG. 39 is a perspective view of a cassette having a flange according to the present invention.

While described as a flange 336, the flange in one embodiment is considered a canopy that has a top that extends into arcuate sidewall that runs along the perimeter 338 of the cassette 50 as best shown in FIG. 39. In this embodiment rib elements 339 form part of, and support, the top portion of the flange 336.

Figure 34:
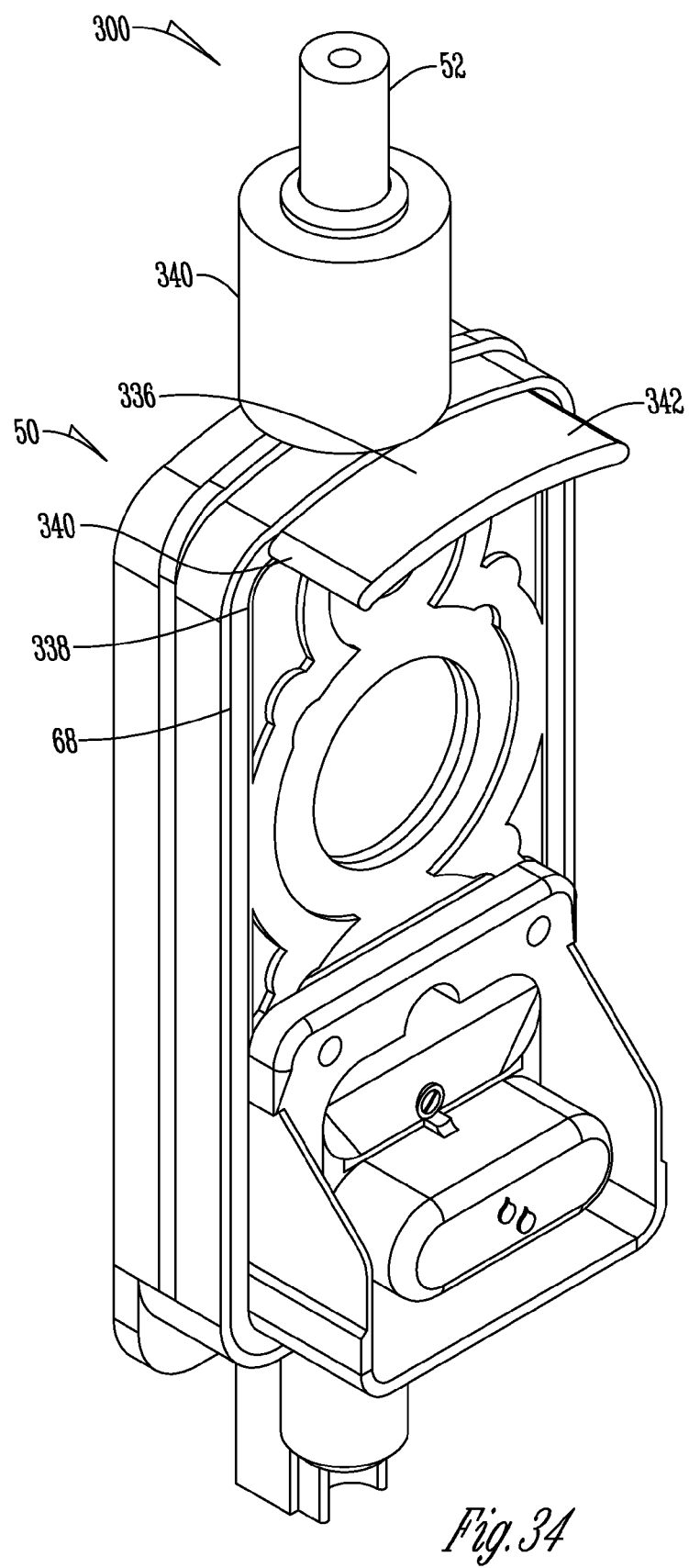
FIG. 34 is a perspective view of a cassette having a flange of the present invention.
Figure 35:
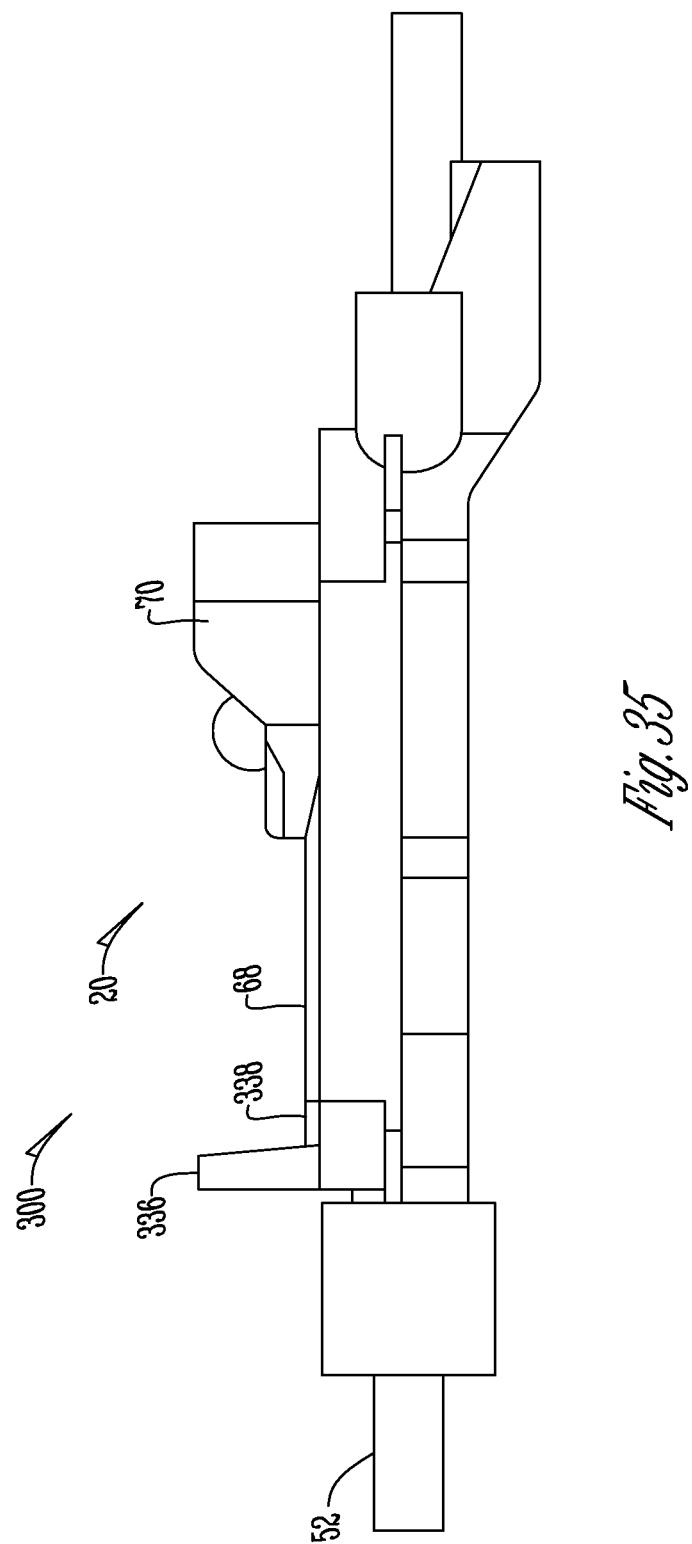
FIG. 35 is a plan view of a cassette having a flange of the present invention.
Figure 36:
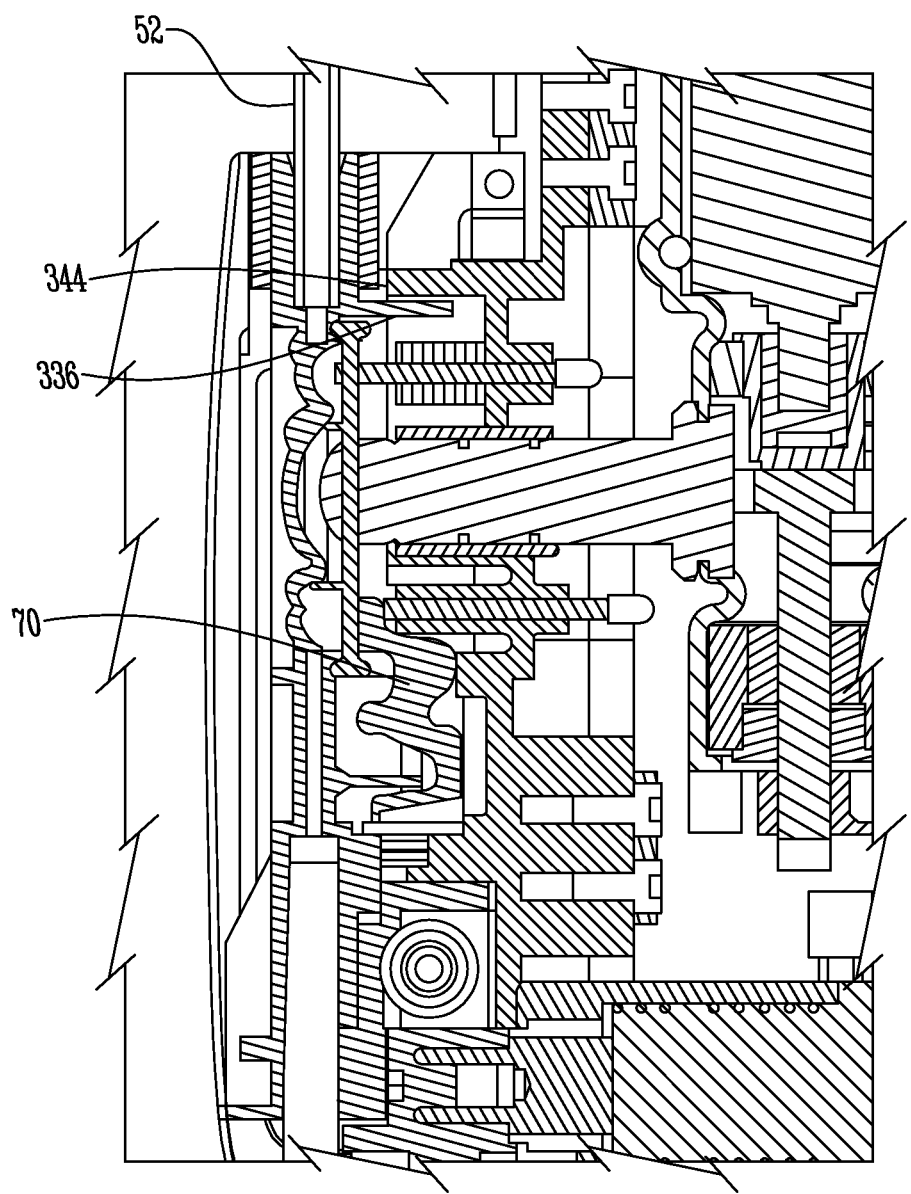
FIG. 36 is a sectional view of a cassette having a flange of the present invention within a loader in a fully closed position.
Figure 37:
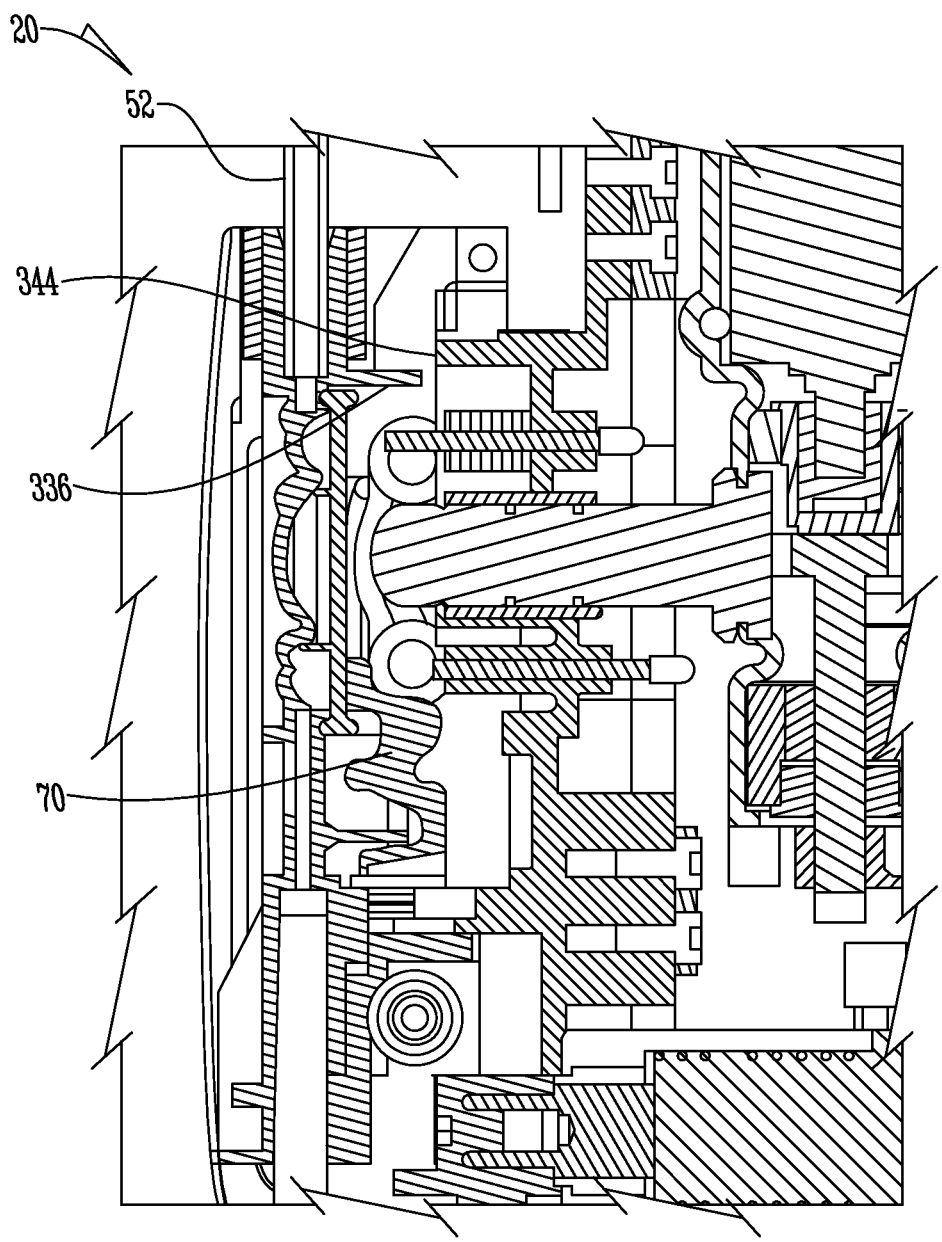
FIG. 37 is a sectional view of a cassette having a flange of the present invention within a loader in a partially opened position.
Figure 38:
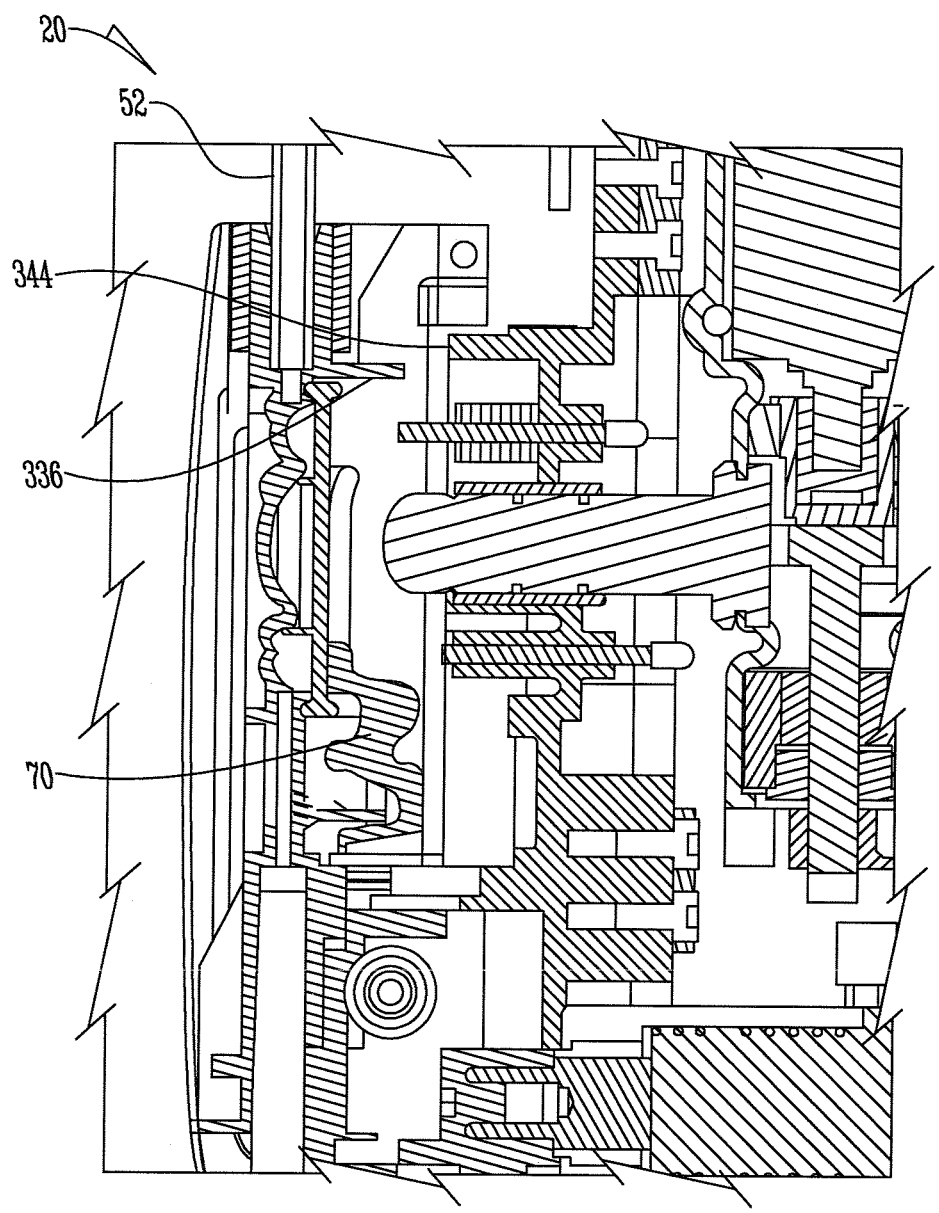
FIG. 38 is a sectional view of a cassette having a flange of the present invention within a loader in a fully opened position.

Alternatively the flange 336 is an arcuate section only on the top perimeter 338 of the cassette 50 as shown in FIG. 34. Thus the flange surrounds the perimeter of the cassette 50 or the like that extends from the cassette 50. Further in one embodiment notches 340 are disposed in the outer surface 342 of the flange 338 to ensure the flange clears an interior flange 344 formed by a motor saddle, upper chassis or the like. In this manner the cassette 50 cannot be pulled out of the loader 20 until the motor saddle 344 and the flange 336 are cleared as best shown in FIGS. 34 and 35.

Again, similar to the embodiment where the collar 320 is placed on the inlet 52 the flange 336 prevents the cassette 50 from being removed from the cassette loader 20 until the loader 20 is in a fully opened position. Specifically, the flange 336 is of size and shape to have a tolerance slightly less than the opening created when the cassette loader 20 is in a fully opened condition. For example the flange 336 can be approximately the same width as the cassette 50 and extend outwardly (upwardly) from the inner surface 68 of the cassette to a height approximately equal to the height of the flow stop 50 or any wall(s) surrounding the flow stop on the outlet end of the cassette. By preventing the cassette 50 from being removed from the cassette loader 20 until the loader 20 is in a fully opened position, the premature removal of the cassette 50 and inadvertent opening of the flow stop 70 is prevented.

Thus, presented is a medical pump with multiple preventing means 300 that prevent the free flow of fluid during the removal of the cassette 50. One skilled in the art will appreciate that the preventing means described herein can also help ensure proper alignment and trouble-free installation of the cassette 50 in the loader 20. The preventing means are simple to manufacture, inexpensive and prevent inadvertent free flow. Thus, at the very least all of the stated objectives have been met.

What is claimed is:

1. A fluid delivery device removably insertable into a loader opening of a loader of a medical pump to control fluid flow in the medical pump comprising:
   an elongated main body including an inlet, an outlet, and a fluid passage extending from the inlet to the outlet;
   a flow stop pivotally mounted to the main body for selectively allowing and stopping fluid flow from the fluid passage to the outlet, and
   a collar element having a base leg that surrounds the inlet, the collar element being adapted to be inserted through the loader opening and reside inside the loader when the loader is in a fully open position, and then once inserted, providing mechanical resistance to withdrawal of the fluid delivery device from the loader by engagement of the collar element with a portion of the medical pump adjacent to the loader unless the loader is in a fully open position.

2. The fluid delivery device of claim 1 wherein the fluid delivery device is a cassette.

3. The fluid delivery device of claim 1 wherein the collar element is T-shaped.

4. The fluid delivery device of claim 1 wherein the portion of the medical pump includes an indicator window that has a window body adjacent to the loader and the collar element engages the indicator window when a user attempts to remove the fluid delivery device from the medical pump.

5. The fluid delivery device of claim 1 wherein the collar element is T-shaped having the base leg and a cross member connected to the base leg.

6. The fluid delivery device of claim 5 wherein the base leg of the collar element has an opening disposed therein that receives the inlet of the fluid delivery device.

7. The fluid delivery device of claim 5 wherein the cross member is approximately as long as the fluid delivery device is wide such that the cross member engages the portion of the medical pump when the loader is not fully open.

8. The fluid delivery device of claim 5 wherein the inlet has a protrusion extending from an exterior surface of the inlet and a retention notch adjacent the opening in the base leg of the collar element receives the protrusion so to retain the collar element on the inlet.

9. The fluid delivery device of claim 1 wherein the collar element has a hollow interior defining an opening with a sidewall having a retention notch formed therein for receiving and engaging a protrusion of the inlet.

10. The fluid delivery device of claim 9 wherein the opening of the collar element is tapered and narrows toward the retention notch.

11. The fluid delivery device of claim 9 wherein a lead-in lip element extends from the sidewall into the opening of the collar element at a location adjacent to the retention notch so that an external force must be applied to force the protrusion on the inlet over the lip element to reach the retention notch.

12. The fluid delivery device of claim 9 wherein the retention notch defines a ledge that is perpendicular to a longitudinal axis of the opening so as to inhibit longitudinal movement of the collar element with respect to the inlet in at least one direction.

* * * * *